United States Patent [19]

Misiura et al.

[11] Patent Number: 5,864,032

[45] Date of Patent: *Jan. 26, 1999

[54] PHOSPHORAMIDITE DERIVATIVES, THEIR PREPARATION AND THE USE THEREOF IN THE INCORPORATION OF REPORTER GROUPS ON SYNTHETIC OLIGONUCLEOTIDES

[75] Inventors: Konrad Misiura, Lodz, Poland; Michael J. Gait, Cambridge, Great Britain

[73] Assignee: Amersham International plc, Buckinghamshire, England

[ * ] Notice: The term of this patent shall not extend beyond the expiration date of Pat. No. 5,567,811.

[21] Appl. No.: 406,700

[22] Filed: Mar. 20, 1995

Related U.S. Application Data

[62] Division of Ser. No. 946,477, filed as PCT/GB91/00713 May 3, 1991, Pat. No. 5,567,811.

[30] Foreign Application Priority Data

May 3, 1990 [GB] United Kingdom ............... 9009980

[51] Int. Cl.⁶ .................. C07H 21/00; C07H 19/00
[52] U.S. Cl. .................. 536/25.34; 536/25.32; 536/23.1; 435/6
[58] Field of Search ............... 536/25.34, 26.6, 536/25.32, 23.1; 435/6; 935/78

[56] References Cited

PUBLICATIONS

Alves et al., Tetrahedron Letters, 30(23):3089–3092, 1989.
Misiura et al., Nuc. Acids Res., vol. 18, No. 15, pp. 4345–4354 (1990).
Nelson et al., Nuc. Acids Res., vol. 17, No. 18, pp. 7179–7186 (1989).

Primary Examiner—George G. Elliott
Assistant Examiner—Scott W. Houtteman
Attorney, Agent, or Firm—Wenderoth, Lind & Ponack

[57] ABSTRACT

Phosphoramidite derivatives of formula (V),

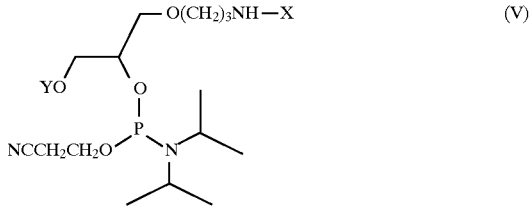

wherein X is biotin and Y is a protecting group. There may be a linker arm, of variable length, between X and the rest of the molecule. Examples of the protecting group Y include 4,4'-dimethoxytrityl, trifluoroacetyl and fluorenylmethoxycarbonyl (Fmoc). The phosphoramidite derivatives are useful in single or multiple labelling of synthetic oligonucleotides. Process for the preparation of these phosphoramidite derivatives are also disclosed.

6 Claims, 9 Drawing Sheets

PHOSPHORAMIDITE DERIVATIVES, THEIR PREPARATION AND THE USE THEREOF IN THE INCORPORATION OF REPORTER GROUPS ON SYNTHETIC OLIGONUCLEOTIDES

This is a Rule 60 divisional application of Ser. No. 07/946,477, filed as PCT/GB91/00713 May 3, 1991, now U.S. Pat. No. 5,567,811.

This invention relates to certain novel phosphoramidite derivatives, particularly biotinyl and phosphotyrosinyl phosphoramidite derivatives, which are useful in the incorporation of single or multiple reporter groups on synthetic oligonucleotides. Processes for the preparation of these phosphoramidite derivatives are also disclosed.

Chemically labelled oligonucleotides are today commonly used as hybridisation probes for the detection of specific gene sequences, including those associated with human genetic diseases. Such probes may be labelled with biotin and this is highly detectable due to its affinity for binding to the proteins avidin and streptavidin. Biotin can thus in some circumstances provide a safer and more convenient form of labelling than would the use of a radioactive label (such as $^{32}P$). In addition to hybridisation probes, biotin-labelled synthetic DNA (particularly 5'-biotinylated oligonucleotides) has found uses in ligase-mediated gene detection, direct di-deoxy sequencing following the polymerase chain reaction and the non-radioactive sequencing of DNA. However, the use of such materials has heretofore been restricted by the lack of an efficient and straightforward method for their production.

Numerous methods are known for the attachment of a single biotin moiety or other single reporter groups to the 5'-end of a synthetic oligodeoxyribonucleotide. Most of these involve the use of a linker phosphoramidite or H-phosphonate as the final coupling step in machine-aided assembly of the oligonucleotide [1–4]. After deprotection, an amino, thiol, or other functional group is generated at the 5'-end of the oligonucleotide and this group must then be reacted with an activated biotin derivative in a separate step.

For the attachment of multiple biotins and other labels, the most common procedures involve the preparation of a nucleoside derivative specially functionalised on the heterocyclic base to give a reactive functional group upon deprotection. The functionalised nucleoside is Incorporated either enzymatically[5,6] or chemically as a phosphoramidite derivative[7,8]. Once again an extra step is necessary in order to convert the functional groups into the appropriate polybiotinylated species. More recently, Roget et al[9] have shown that it is possible to use 4-N-(6-N-biotinylaminohexyl)-2$^i$-0-deoxycytidine (or -5-methyl-2'-deoxycytidine) derivatised as a phosphoramidite in machine-aided assembly of oligonucleotides to generate, upon deprotection, biotinylated nucleotide tails on the 5'-end of oligonucleotides. A 45-mer oligonucleotide tailed in this way is claimed to be more sensitive in in situ hybridisation using a streptavidin-alkaline phosphatase detection system than the same 45-mer tailed at the 3'-end with biotin dUTP by an enzymatic method[10], although no quantitation was reported.

Cytidine derivatives functionalised on the heterocycle with biotin are not particularly conveniently prepared in that the 4-thiodeoxynucleoside starting materials are expensive. Moreover, the use of oligonucleotide tails may limit the stereochemical accessibility of the biotin moieties or alter the hybridisation properties of the oligonucleotide probe to which it is attached. Thus the use of a much simpler, non-nucleosidic linker phosphoramidite reagent capable of allowing the incorporation of multiple biotins or other reporter groups would be desirable.

Recently, Nelson et al.[11] have reported that a 3-amino-1,2-propanediol unit can be functionalised to provide a phosphoramidite that can be used in oligonucleotide assembly. After deprotection, the oligonucleotide contains a 5'-tail of aliphatic primary amino groups on a repeating branched 3-carbon backbone. Whereas five such units can be efficiently assembled at the 5'-end of an oligonucleotide, only 65% of the amino groups could be functionalised subsequently with biotin, however. Very recently, Haralambidis et al.[12] have reported the incorporation of up to 10 biotin residues on the 3'-end of an oligonucleotide by means of a combination of synthetic peptide and oligonucleotide chemistry on solid-phase. A disadvantage of this approach, however, is that two different machines are required for assembly of the peptide-oligonucleotide composite. In addition, it is necessary for the biotin to be conjugated after assembly of the polyamide chain.

In the case of biotin and other chemically stable reporter groups, it would be advantageous to incorporate the reporter group directly into the phosphoramidite derivative rather than to have to rely on post-assembly functionalisation. While there have been two recently published reports of biotinyl linker phosphoramidites having been used to attach single biotin moieties to the 5'-end of synthetic oligonucleotides[13,14], to our knowledge no biotinyl linker phosphoramidite has been described which is capable of-allowing incorporation of multiple biotins into a synthetic oligonucleotide.

The object of the present invention is to facilitate the more convenient usage and synthesis of a biotinyl linker phosphoramidite and also a linker phosphoramidite containing the alternative reporter group, phosphotyrosine, which has not hitherto been used in connection with nucleic acid probes.

According to the present invention, there is provided a phosphoramidite derivative of the following formula:

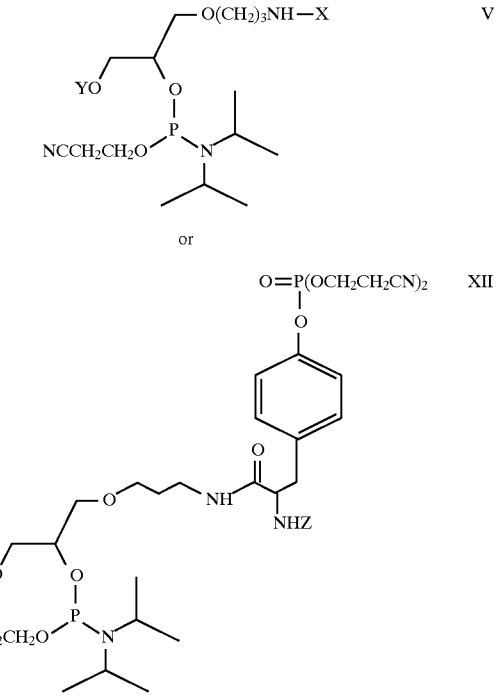

wherein
X=a reporter group, and
Y and Z=protecting groups.

The reporter group (X) may comprise any hapten or other detectable moiety. Examples include: biotin, dinitrophenyl, dansyl and fluoresceinyl. There may be a linker arm, of variable length, between the reporter group and the rest of the molecule. The protecting groups (Y and Z) may comprise, for example, 4,4'-dimethoxytrityl, trifluoroacetyl or fluorenylmethoxycarbonyl (Fmoc).

According to the present invention there is also provided a method for the production of the above biotinyl phosphoramidite derivative (V) and which comprises:

i) Reaction of solketal with acrylonitrile to form the addition product, 2-cyanoethyl solketal (I):

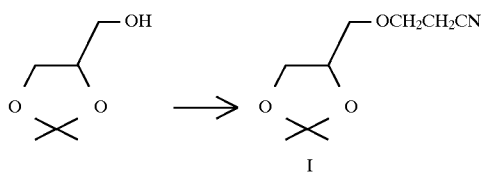

ii) Reduction of the resultant compound (I) to form 3-aminopropyl solketal (II):

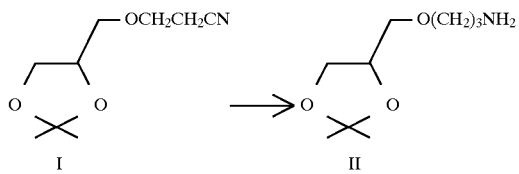

iii) Reaction of the resultant compound (II) with biotin N-hydroxysuccinimide to form N-biotinyl-3-aminopropyl solketal (III):

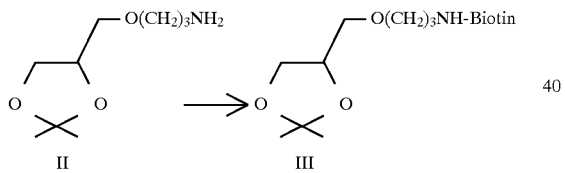

iv) Reaction of the resultant compound (III) with 4,4'-dimethoxytrityl chloride to form 1-0-(4,4'-dimethoxytrityl)-3-0-(N-biotinyl-3-aminopropyl) glycerol (IV):

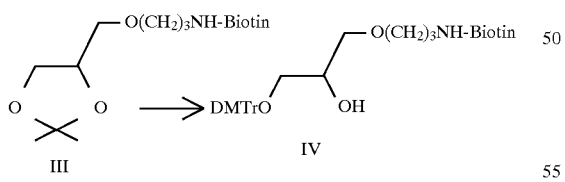

v) Phosphitylation of the resultant compound (IV) to produce the desired biotinyl phosphoramidite derivative (V):

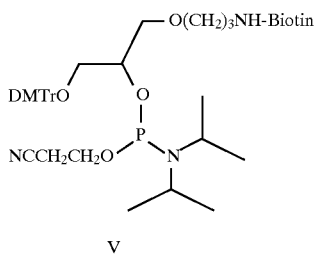

wherein DMTr=4,4'-dimethoxytrityl.

According to the present invention there is also provided a method for the production of the above phosphotyrosinyl phosphoramidite derivative (XII) and which comprises:

i) Reaction of L-tyrosine benzyl ester with 9-fluorenylmethylchloroformate to form N-fluorenylmethoxycarbonyl-L-tyrosine benzyl ester (VI):

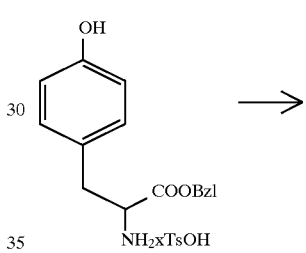

ii) Phosphitylation of the resultant compound (VI), followed by oxidation to form N-fluorenylmethoxycarbonyl-0-[bis(2-cyanoethyl) phosphate]-L-tyrosine benzyl ester (VII):

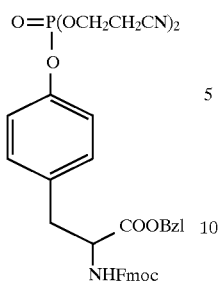

VII

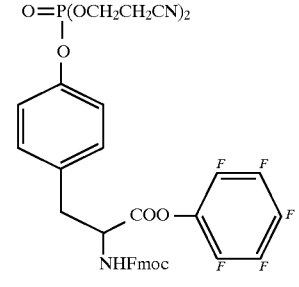

IX iii) Debenzylation of the resultant compound (VII) to form N-fluorenylmethoxycarbonyl-0-[bis(2-cyanoethyl) phosphate]-L-tyrosine (VIII):

v) Coupling the resultant compound (IX) to 3-aminopropyl solketal (II), removing the isopropylidene group from the resultant solketal derivative, followed by reaction of the product with 4,4'-dimethoxytrityl chloride and then phosphitylation of the product thereof to produce the desired phosphotyrosinyl phosphoramidite derivative (XII):

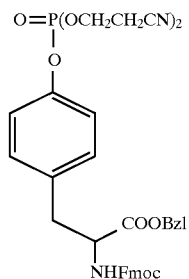

VII

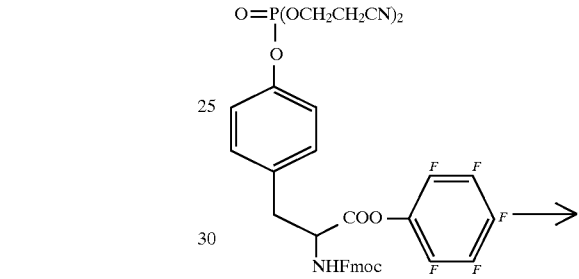

IX

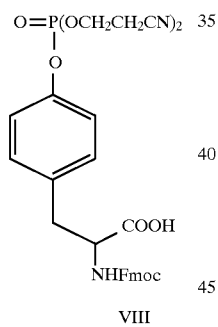

VIII

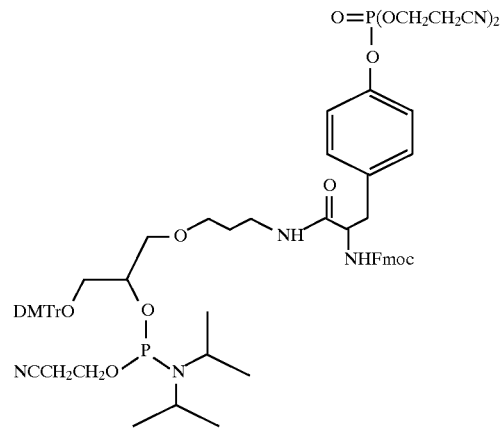

XII iv) Reaction of the resultant compound (VIII) with pentafluorophenol to form the corresponding pentafluorophenyl derivative (IX):

wherein DMTr=4,4'-dimethoxytrityl and

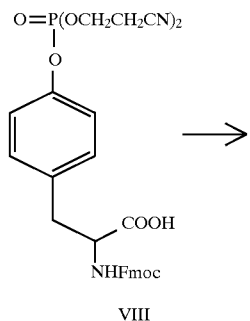

VIII

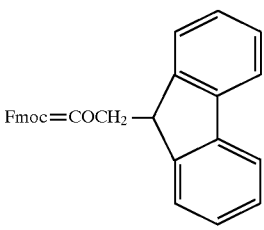

According to a still further embodiment the present invention provides a method for the single or multiple labelling of synthetic oligonucleotides and which comprises the use of the aforementioned biotinyl phosphoramidite derivative (V) or phosphotyrosinyl phosphoramidite derivative (XII). It is to be understood that the incorporation of the single or multiple label may occur at either the 5' end or the 3'end of the oligonucleotide or at any point along the chain.

A variety of uses are envisaged for the phosphoramidite derivatives. These include use for preparing oligonucleotides which may be used as hybridisation probes; for the capture of nucleic acids onto solid support matrices resulting from solid phase or solution phase hybridisation reactions; as primers in the polymerase chain reaction (PCR); as primers in nucleic acid sequencing reactions; in the production of affinity matrices for the purification of DNA binding proteins and other biomolecules; in the production of affinity matrices for the detection of nucleic acid sequences; as a means of monitoring incorporation reactions; in producing a random selection of labelled probes for the detection of the total nucleic acid content of samples by hybridisation; in a sandwich hybridisation system where one labelled probe acts as a capture and a probe with an alternative label acts as a reporter; for providing a biotinylated or haptenylated oligonucleotide for use in any DNA manipulation protocol; in cloning recombinant DNA and in in vitro mutagenesis.

The phosphoramidite derivatives of this invention contain a repeating linker unit and, in both cases, this comprises a simple 3-carbon glyceryl backbone which gives maximum flexibility as well as good aqueous solubility properties. The preparation of the compounds will now be described in greater detail and with reference to Reaction Scheme 1 (biotinyl phosphoramidite) and Reaction Scheme 2 (phosphotyrosinyl phosphoramidite) respectively.

A=1 biotin
B=2 biotins
C=4 biotins
D=8 biotins
E=4 biotins spaced with 3 thymidines
F=Probe labelled directly with horseradish peroxidase.

Figure 11:
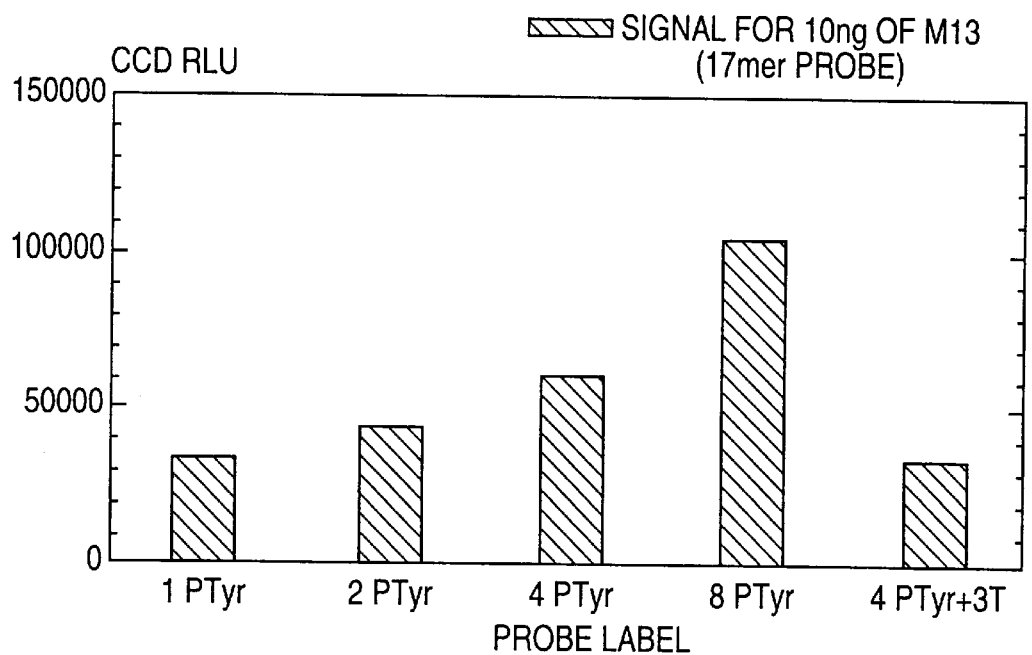

FIG. 11 shows signal strength for ECL detection of 10 ng of M13 DNA for each of five phosphotyrosinylated probes.

A=1 phosphotyrosine
B=2 phosphotyrosines
C=4 phosphotyrosines
D=8 phosphotyrosines
E=4 phosphotyrosines spaced with 3 thymidines.

Scheme 1

Reaction of readily available solketal with acrylonitrile in the presence of sodium hydride in tetrahydrofuran afforded the addition product, 2-cyanoethyl solketal (I), in 79% yield. Reduction of nitrile (I) required carefully controlled conditions since it was found that the use of strong reductants (such as lithium aluminium hydride) cause preferential elimination. Best results were found using sodium borohydride in the presence of cobalt (II) chloride in methanolic solution [15] to afford. 3-aminopropyl solketal which was purified by distillation in 43% yield. Reaction of amine (II) with biotin N-hydroxysuccinimide in DMF solution gave N-biotinyl-3-aminopropyl solketal (III) in 89% yield.

Biotin derivative (III) was treated with a mixture of 1M hydrochloric acid and tetrahydrofuran (1:1) to remove the isopropylidine group and, without isolation, the product was reacted with 4,4'-dimethoxytrityl chloride in anhydrous pyridine to give 1-0-(4,4'-dimethoxytrityl)-3-0-(N-biotinyl-3-aminopropyl)glycerol (IV) which was purified by silica column chromatography in 63% yield. Phosphitylation of compound (IV) was carried out using an equimolar proportion of 2-cyanoethyl N,N-diisopropylaminochlorophosphite[16] in tetrahydrofuran in the presence of N,N-diisopropylethylamine. Under these conditions, the predominant product was the desired singly phosphitylated product, 1-0-(4,4'-dimethoxytrityl)-3-0-(N-biotinyl-3-aminopropyl)glyceryl 2-0-(N,N-diisopropylamino)phosphite (V), which was readily separated by silica column chromatography in 58% yield. $^{31}$P nmr of compound V showed just four peaks of approximately equal intensity corresponding to the four possible diastereomers. Analytical reversed-phase HPLC showed more than 90% of the UV absorption in two closely eluting peaks each presumably corresponding to a pair of diastereomers.

Starting compound IV was also recovered as a later eluting fraction from the silica column in 32% yield. A small amount of doubly phosphitylated product was observed in the crude reaction product, the formation of which was considerably exacerbated by the use of excess phosphitylating agent. $^{31}$P nmr evidence suggested that this contaminant contained one phosphite moiety attached to the biotin ring at N-3, which is in line with the findings of Alves et al[13].

Scheme 2

To prepare a suitable phosphoramidite derivative containing tyrosine phosphate, it was necessary to consider the question of protection of the phosphate group of tyrosine. By analogy with nucleoside phosphate derivatives, it was thought that bis(2-cyanoethyl) protection should afford sufficient stability under acidic conditions yet should be removable with aqueous ammonia under conditions needed to remove base protecting groups. For N-protection, the fluorenylmethoxycarbonyl group was chosen[19].

Reaction of L-tyrosine benzyl ester with 9-fluorenylmethyl-chloroformate in pyridine at 0° C. afforded after crystallisation an 84% yield of N-fluorenylmethoxycarbonyl-L-tyrosine benzyl ester (VI). Phosphitylation of compound VI with bis(2-cyanoethyl)-N, N-diisopropylaminophosphine in acetonitrile in the presence of tetrazole followed by oxidation with 3-chloroperbenzoic acid gave an 86% yield of crystalline N-fluorenylmethoxycarbonyl-0-[bis(2-cyanoethyl) phosphate]-L-tyrosine benzyl ester (VII). Debenzylation of compound VII was accomplished with hydrogen (Pd/C). Concomitant loss of the fluorenylmethoxycarbonyl group was minimised by use of ethyl acetate as a co-solvent with ethanol. Small amounts of liberated dibenzofulvene were removed by diethyl ether extraction and the desired N-fluorenylmethoxycarbonyl-0-[bis(2-cyanoethyl) phosphate]-L-tyrosine (VIII) was purified by extraction from acidic solution into ethyl acetate and isolated in 65% yield.

The tyrosine phosphate derivative VIII when treated with a mixture of 0.1M hydrochloric acid and tetrahydrofuran (1:1) at room temperature for 3 hours gave less than 5% loss of the phosphate group. Treatment of compound VIII with concentrated ammonia in a sealed tube for 5 hours at 60° C. gave rise to complete removal of both 2-cyanoethyl groups with only a trace of loss of phosphate.

Reaction of compound VIII with pentafluorophenol in the presence of dicyclohexylcarbodiimide in dioxane solution gave the corresponding pentafluorophenyl derivative (IX) in 82% yield. IX was coupled to 3-aminopropyl solketal (II) in DMF solution to give after silica column chromatography an 86% yield of N-fluorenylmethoxycarbonyl-0-[bis(2-cyanoethyl) phosphate]-L-tyrosinyl-3-aminopropyl solketal (X). The isopropylidene group of the solketal derivative X was removed using 1M hydrochloric acid/tetrahydrofuran and without isolation the product was reacted in pyridine solution with 4,4'-dimethoxytrityl chloride to give after silica column chromatography 1-0-(4,4'-dimethoxytrityl)-3-0-(N-[N-fluorenylmethoxycarbonyl-0-[bis(2-cyanoethyl) phosphate]-L-tyrosinyl]-3-aminopropyl)glycerol (XI) in 70% yield. Phosphitylation of compound XI by 2-cyanoethyl N,N-diisopropylaminochlorophosphite in the presence of N,N-diisopropylethylamine gave after silica column chromatography the corresponding 2-0-(N,N-diisopropylamino)(2-cyanoethyl)phosphite derivative (XII) as a solid foam in 44% yield. The $^{31}P$ nmr spectrum of compound XII showed a doublet at δ–148.65 and 148.64 corresponding to the tyrosyl phosphate and three peaks at δ7.41, 7.68 and 7.96 in the ratio of 1:1:2. These latter 3 signals are presumably accounted for by only partial resolution of the expected 4 diasteromers due to chirality at the C-2 of the glyceryl moiety and the P of the phosphite group.

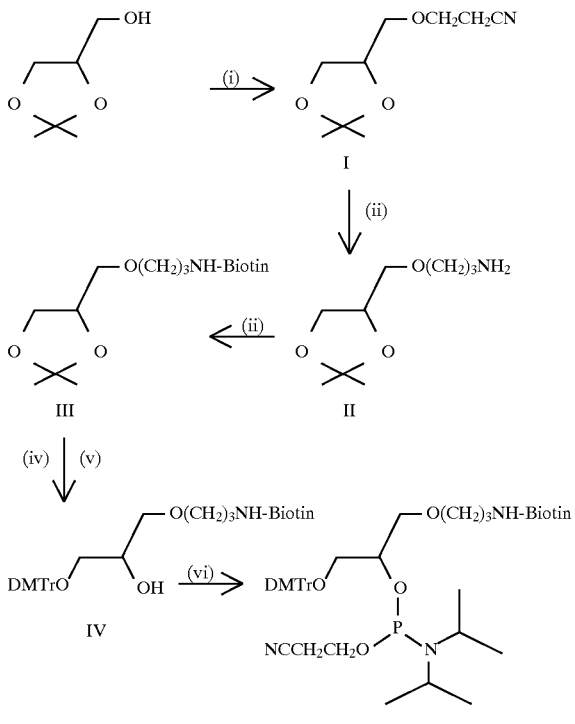

Scheme 1.
Synthesis of biotinyl phosphoramidite (i) NaH, CH$_2$=CH$_2$CN, THF
(ii) CoCl$_2$, NaBH$_4$, MeOH
(iii) Biotin-NHS, DMF
(iv) HClaq, THF
(v) DMTrCl, Py
(vi) ClPN($^i$Pr)$_2$OCH$_2$CH$_2$CN, CH$_3$CH$_2$N($^i$Pr)$_2$, THF

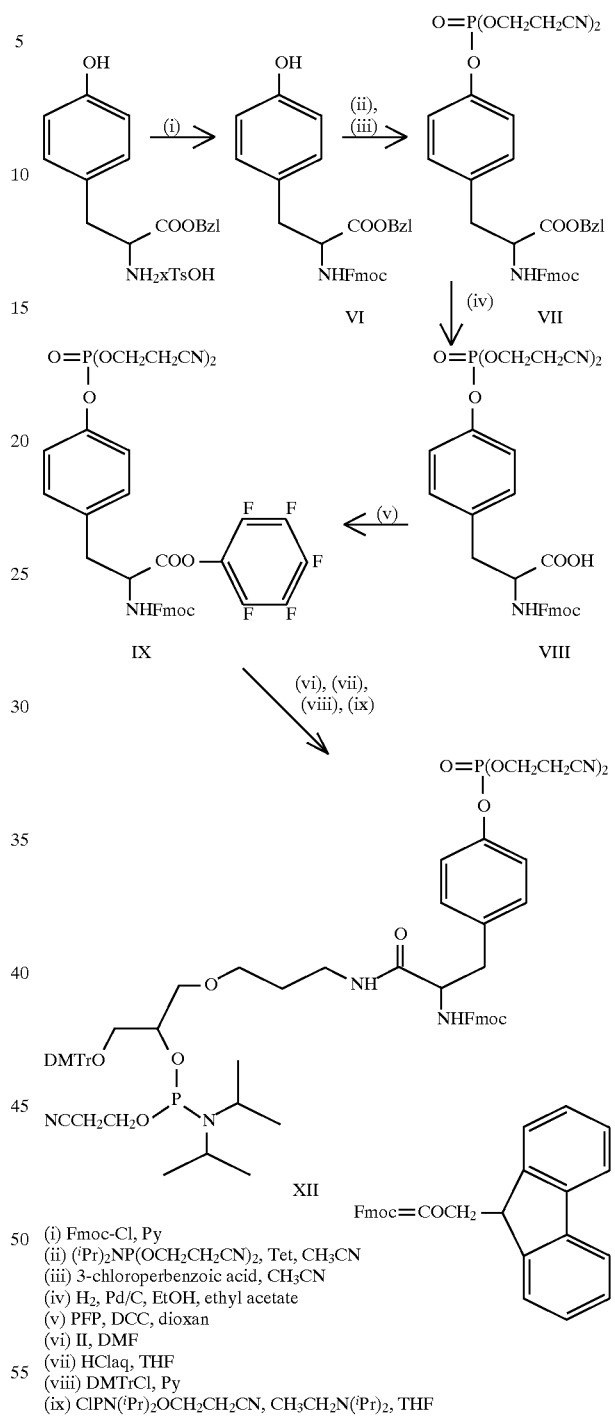

Scheme 2.
Synthesis of phosphotyrosinyl phosphoramidite (i) Fmoc-Cl, Py
(ii) ($^i$Pr)$_2$NP(OCH$_2$CH$_2$CN)$_2$, Tet, CH$_3$CN
(iii) 3-chloroperbenzoic acid, CH$_3$CN
(iv) H$_2$, Pd/C, EtOH, ethyl acetate
(v) PFP, DCC, dioxan
(vi) II, DMF
(vii) HClaq, THF
(viii) DMTrCl, Py
(ix) ClPN($^i$Pr)$_2$OCH$_2$CH$_2$CN, CH$_3$CH$_2$N($^i$Pr)$_2$, THF The phosphoramidite (V) was used in the final coupling steps in oligonucleotide assembly by the phosphoramidite procedure[17] using an Applied Biosystems 380B 3-column DNA synthesiser. Three parallel assemblies were carried out of the 17-mer d(GTAAAACGACGGCCAGT) (corresponding to the sequence of the universal M13 sequencing primer[18] with respectively one, two and four extra cycles of coupling with phosphoramidite (V) after the assemblies of the core oligonucleotide 17-mers. The efficiency of addition of phosphoramidite (V) averaged 99% as judged by release of dimethoxytrityl cation before subsequent coupling steps. The final terminal dimethoxytrityl group in assembly was not removed. This was to maintain the terminal primary hydroxyl group in a masked configuration in order to prevent, during subsequent ammonia treatment, attack of the terminal hydroxyl group of the glyceryl moiety on the nearest phosphate linkage giving rise to elimination of the terminal glyceryl unit.

Figure 1:
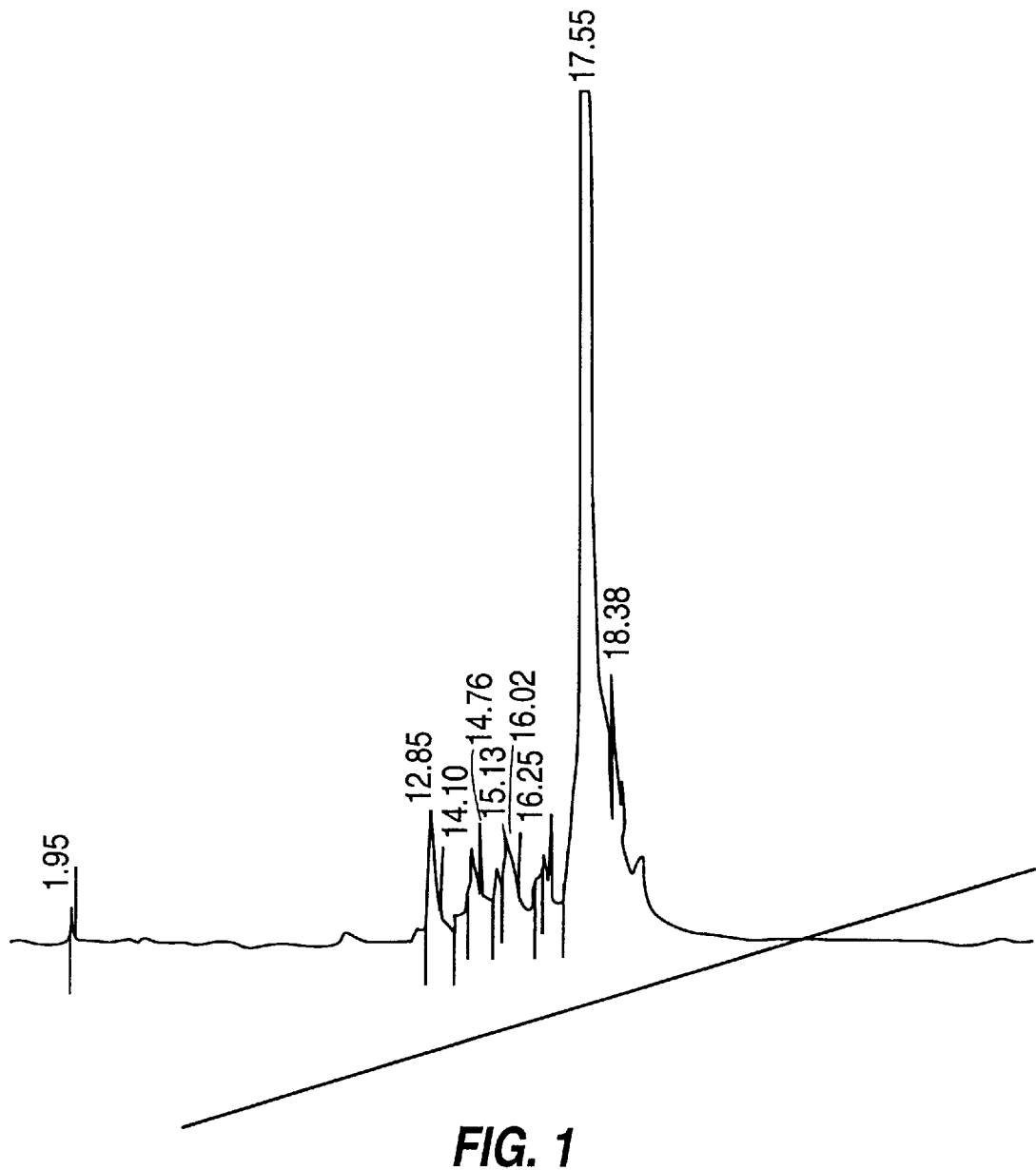
FIGS. 1 to 7 show results for isolation of oligonucleotides as described in Scheme 2, by reverse phase liquid chromatography or preparative polyacrylamide gel electrophoresis.
Figure 2:
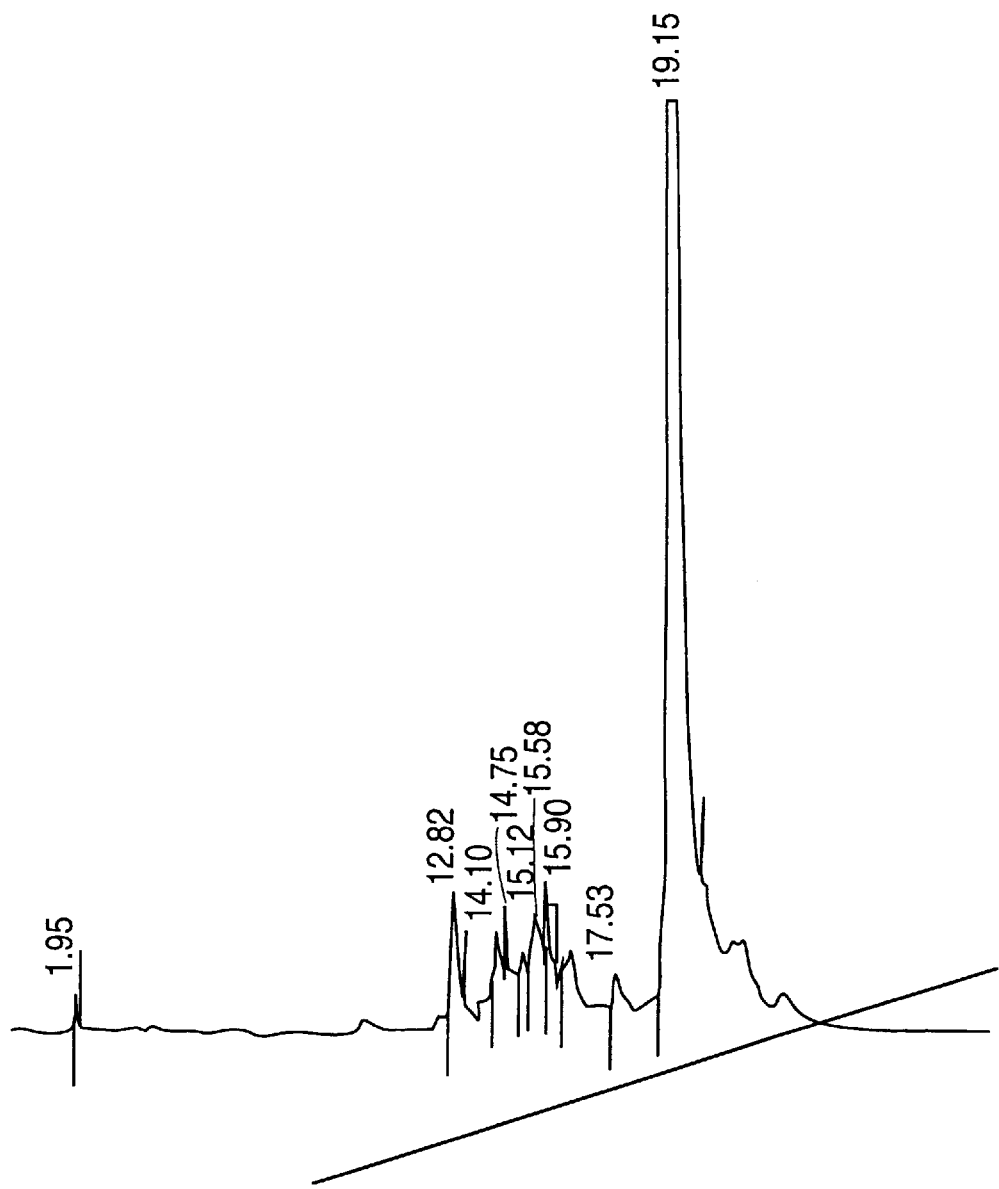
Figure 3:
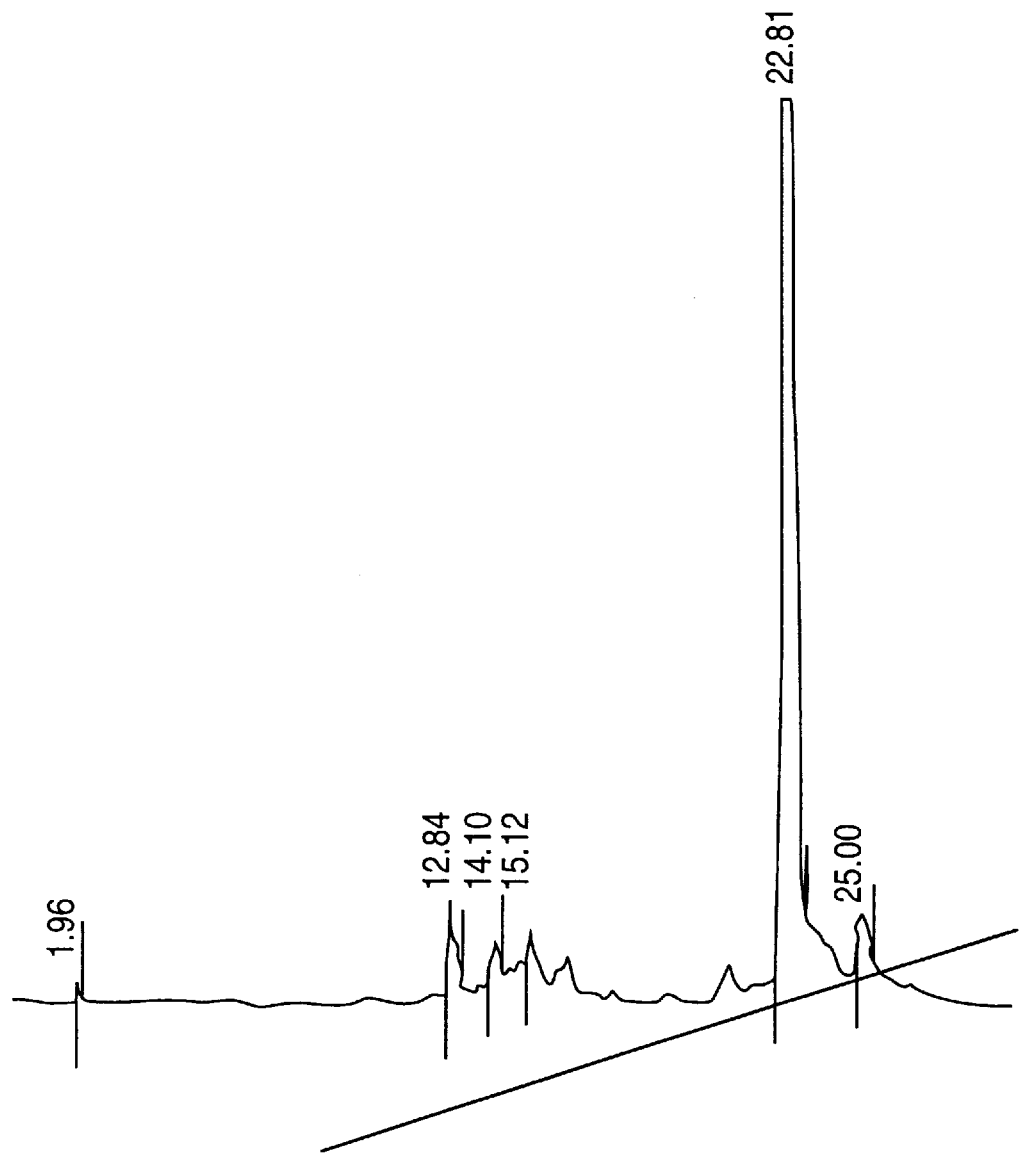
Figure 4:
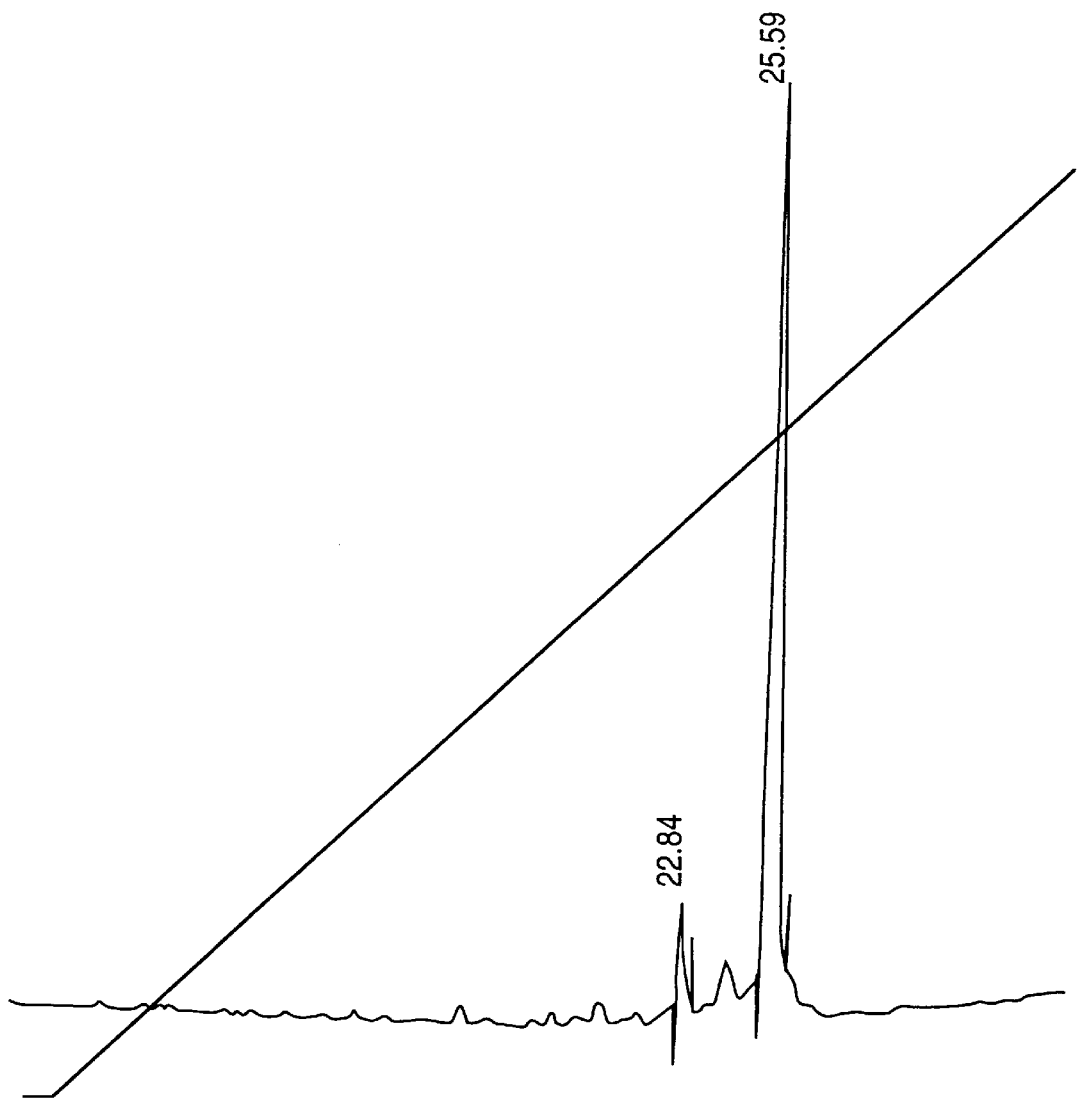
Figure 5:
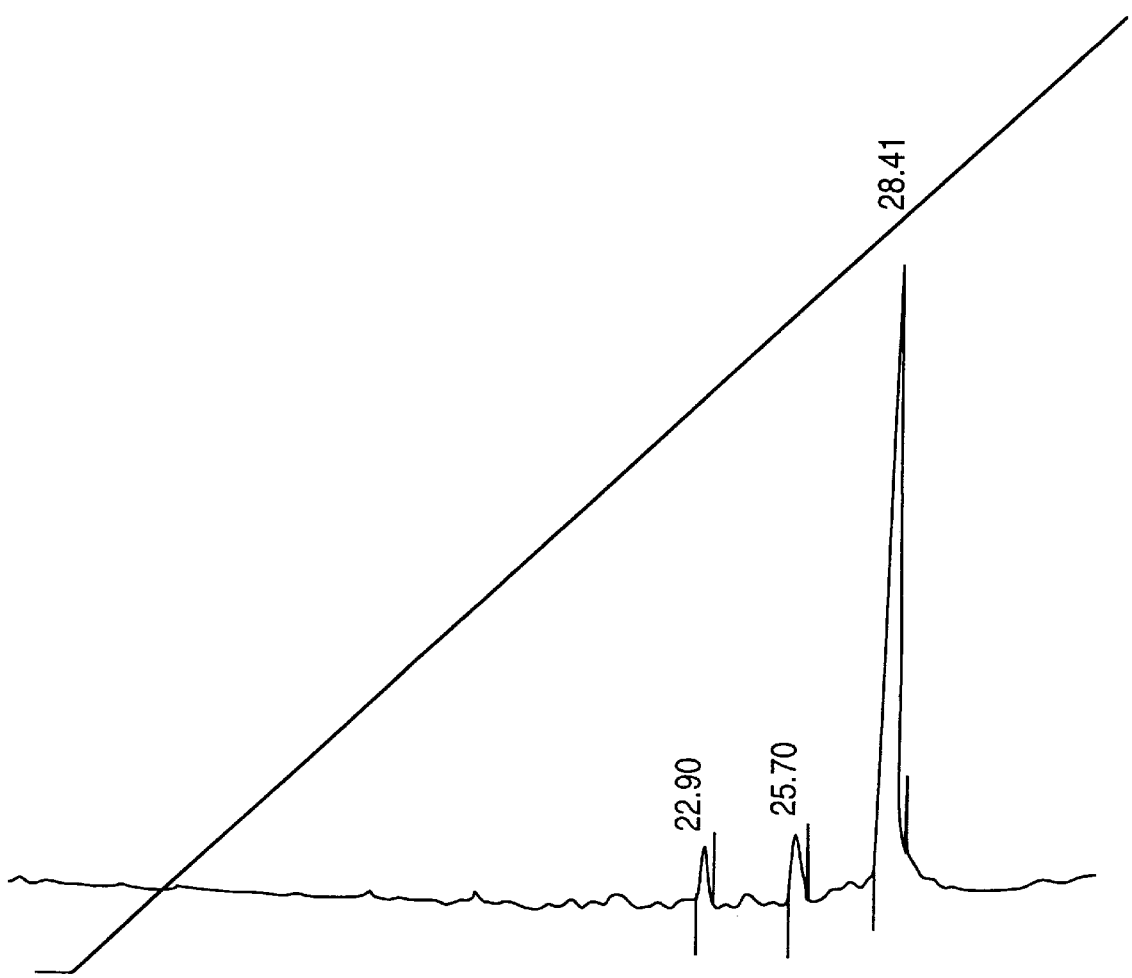
Figure 6:
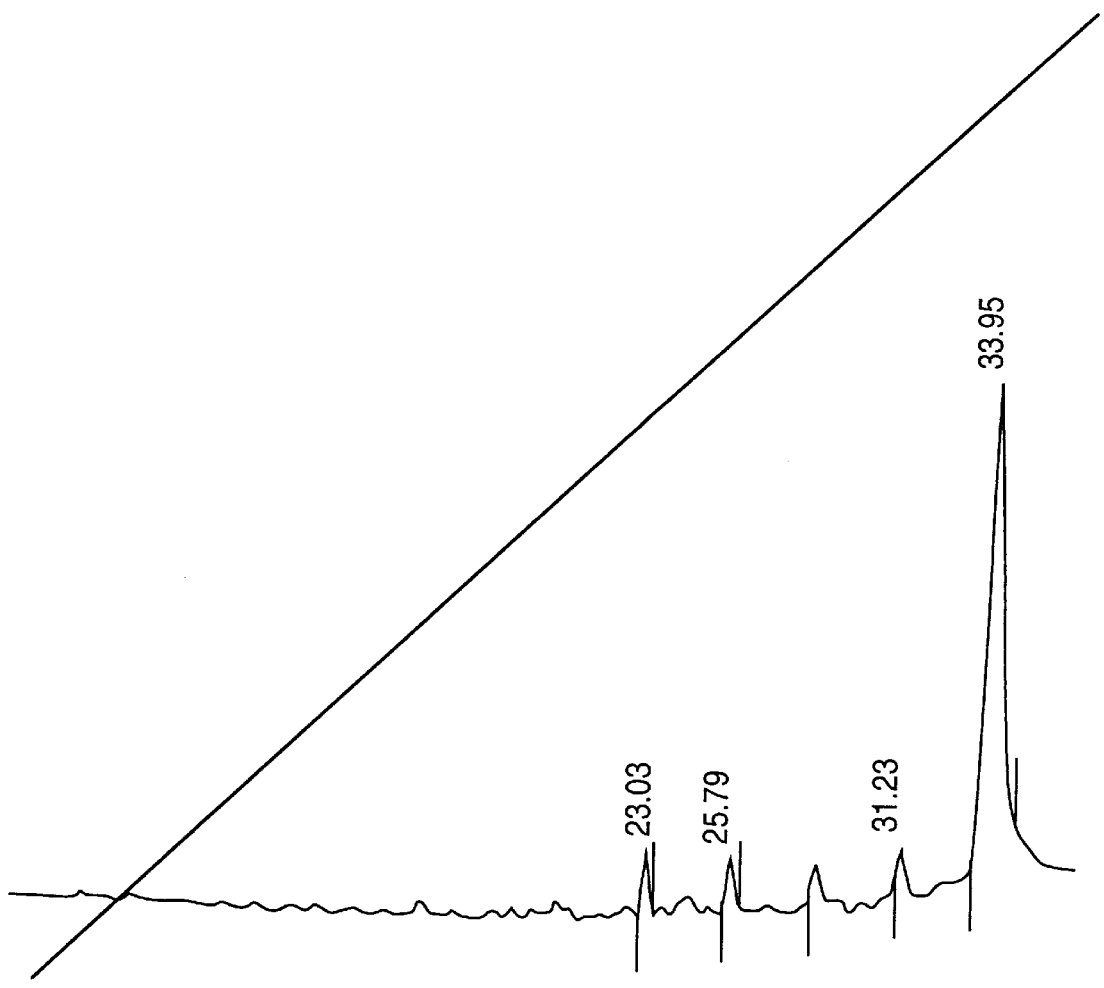
Figure 7:
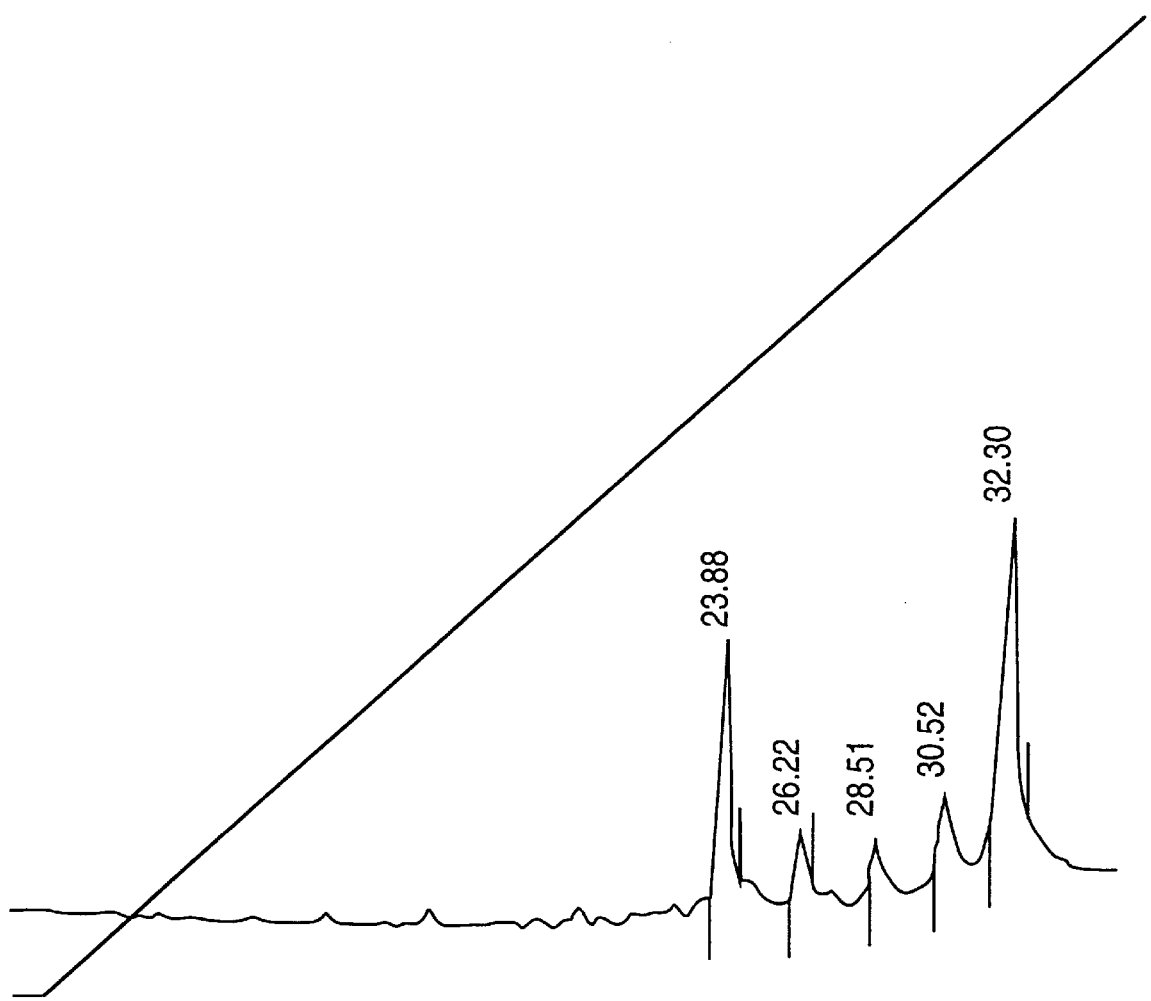

After complete deprotection, the three 17-mers were purified by reversed phase chromatography and in each case a major component corresponding to the desired product was seen (FIGS. 1, 2 and 3). It can be seen that the singly biotinylated 17-mer $(bio)_1$-17 was retarded in mobility compared to an unbiotinylated control. The doubly biotinylated 17-mer $(bio)_2$-17 was further retarded and the quadruply biotinylated 17-mer $(bio)_4$-17 was still further retarded. Thus, reversed phase chromatography is a convenient system for both purification and for assessment of the homogeneity of biotinylated oligonucleotides. Overall isolated yields after assembly and purification were 26, 25 and 19% respectively for $(bio)_1$-17, $(bio)_2$-17 and $(bio)_4$-17 respectively based on the amount of first nucleoside attached to the support.

A 5'-tail of eight biotins was also prepared by assembly of the same 17-mer followed by 8 sequential additions of the biotinyl linker (V) which afforded after deprotection a 19% overall isolated yield of the $(bio)_8$-17 after reversed-phase chromatography. In order to determine the effect of further spacing of biotin residues, another assembly of the 17-mer was carried out followed by four additions of biotin linker interspersed with three thymidyl residues. The isolated yield of (bio-dT)3-bio-17) was 19% after reversed-phase purification.

The phosphotyrosyl linker XII was used in oligonucleotide assembly of the following derivatives of the 17-long M13 primer: $(PTyr)_1$-17, $(PTyr)_2$-17, $(PTyr)_4$-17, the thymidyl spaced derivative $(PTyr-dT)3-PTyr$-17, and $(PTyr)_8$-17. Average coupling yields for the phosphotyrosyl linker as judged by analysis of liberated dimethoxytrityl groups were 96%. In the cases of the first four oligonucleotides, isolation was by ion exchange HPLC (FIGS. 4, 5, 6 and 7) making use of the extraformal negative charges on the phosphotyrosine moieties to aid separation (isolated yields of 16, 8, 13 and 14% respectively), whereas for the $(PTyr)_8$-17 preparative polyacrylamide gel electrophoresis was used (isolated yield 14%).

The present invention is further illustrated by the following Examples.

EXAMPLE 1

Pyridine, acetonitrile and N,N-diisopropylethylamine were dried by distillation from calcium hydride. Tetrahydrofuran and dioxane were dried by distillation from sodium/benzophenone. N,N-dimethylformamide (DMF) was dried by distillation under reduced pressure (18 mm Hg). Biotin N-hydroxysuccinimide was prepared from biotin by the method of Becker et al (20). L-Tyrosine benzyl ester p-toluenesulphonate salt was obtained from Sigma and 9-fluorenylmethyl-chloroformate from Fluka. Bis(2-cyanoethyl)-N,N-diisopropylaminophosphine was obtained from dichloro-N,N-diisopropylaminophosphine (Aldrich) by the method of Uhlmann and Engels (21). Organic solution were dried over anhydrous sodium sulphate. Column chromatography was carried out by the short column method using Kieselgel 60H (Merck).

Melting points were measured on a Koefler hot stage apparatus and are uncorrected. Thin layer chromatography (t.l.c.) was carried out using Kieselgel 60 F254 plates (Merck) with aluminium backing and devolpment with the following solvents: A, chloroform/absolute ethanol (19:1); B, chlorofom/ethanol (9:1); C, chloroform/ethanol (4:1); D, acetonitrile/methanol (4:1); E, methylene chloride/methanol (9:1) containing 1% pyridine; F, chloroform/ethanol (39:1); G, chloroform/ethanol (9:1) containing 2% acetic acid; H, methylene chloride/methanol (19:1); I, methylene chloride/ethyl acetate (1:1) containing 1% 2,6-lutidine. Plates were visualised under shortwave ultraviolet light, with iodine vapour, or by spraying with 2% ethanolic molybdophosphoric acid. Dimethoxytrityl-containing compounds were visualised by exposing the t.l.c plate to vapour of concentrated hydrochloric add. Biotin-containing derivatives were visualised by spraying with a reagent containing p-dimethylaminocinnamaldehyde (22).

Proton nuclear magnetic resonance (nmr) spectra were recorded on a Bruker WM-250 spectrometer (250 MHz) with chemical shifts given relative to tetramethylsilane and $^{31}$P-nmr were recorded on a Bruker AM400 spectrometer (162 MHz) with chemical shifts given relative to trimethyl phosphite. All spectra were taken with compounds as deuterochloroform solutions unless otherwise stated. Mass spectra were recorded on a Kratos model MS 890 spectrometer for fast atom bombardment (FAB) ionisation using 3-nitrobenzylalcohol as matrix and on a Kratos MS 902 spectrometer for electron impact (EI) ionisation.

Reversed-phase h.p.l.c. was carried out on an analytical or a semipreparative $\mu$ Bondapak C18 reversed phase column (Waters) using gradients of buffer A (0.1M ammonium acetate solution) and buffer B (20% buffer A/80% acetonitrile) at flow rates of 1.5 ml/min (analytical runs) or 3 ml/min (purification runs). Ion exchange h.p.l.c was carried out on an analytical Partisphere 5-SAX cartridge (Whatman) using gradients of potassium phosphate buffer (pH 6.3) containing 60% formamide.

2-Cyanoethyl solketal (1)

Solketal (2,2-dimethyl-1,3-dioxolane4-methanol) (26.4 g, 200 mmole) and acrylonitrile (26.4 ml, 400 mmole) were dissolved in dry tetrahydrofuran (500 ml). To the stirred and cooled (waterbath) solution, sodium hydride (0.96 g, 40 mmole) was added in two portions and stirring was continued for 1 hour. Then water (100 ml) was added dropwise and the resultant suspension was concentrated to remove tetrahydrofuran. Water (200 ml) was again added and the mixture was extracted with methylene chloride (2×300 ml). The extracts were dried and concentrated to give an oil (44.06 g) which was distilled under reduced pressure to give the title compound (23.42 g, 79% yield) as an oil (bp. 96°–97° C. at 0.5 mm Hg.).T.l.c. in Solvent A, $R_f$ 0.76. $^1$H nmr, δ:1.35 (s,3H), 1.41 (s,3H), 2.61 (t, J=6.3 Hz, 2H), 3.51–3.58 (m, 2H), 3.69–3.76 (m, 3H), 4.05 (dd, J=8.2 Hz, J=6.4 Hz, 1H), 4.23 (quintet, J=5.5 Hz, 1H). Mass Spectrum (EI), m/z 186 ($M^{+\cdot}$+1).

3-Aminopropyl solketal (II)

2Cyanoethyl solketal (I)(27.75 g 150 mmole) was dissolved in methanol (900 ml) and cobalt(II) chloride.$6H_2O$ (71.37 g, 0.3 mole) was added. To this stirred and cooled (waterbath) solution was added sodium borohydride (56.76 g, 1.5 mole) in two portions (caution, foaming). Stirring was continued for 1 hour and then concentrated ammonia solution (300 ml) was added. The resultant suspension was filtered and concentrated to remove methanol. The mixture was extracted with chloroform (2×300 ml) and the extracts dried and evaporated to give an oil (20.82 g) which was distilled under reduced pressure to yield the title compound (12.12 g, 43% yield) as an oil (bp. 78°–9° C. at 0.5 mm Hg).

T.l.c. in Solvent B, $R_f$ 0.10. $^1$H-nmr, δ: 1.34 (s, 5H), 1.40 (s, 3H), 1.70 (quintet, J 65 Hz, 2H), 2.77 (t, J 6.8 Hz, 2H, 3.38–357 (m, 4H), 3.70 (dd, J=82 Hz, J=6.3 Hz, 1H), 4.03 (dd, J=8.2 Hz,J=6.3 Hz, 1H), 4.24 (quintet, J=5.8 Hz, 1H). Mass Spectrum (EI), m/z 190 (M$^+$·+1).

N-Biotinyl-3-aminopropyl solketal (III)

Biotin N-hydroxysuccinimide ester (3.41 g, 10 mmole) was dissolved in hot dry DMF (40 ml). After cooling, a solution of 3-aminopropyl solketal (11) (2.27 g, 12 mmole) in dry DMF (20 ml) was added dropwise with stirring. The solution was left for 1 hour and then concentrated. The residue was dissolved in chloroform (100 ml) and washed with saturated sodium bicarbonate solution (50 ml). The aqueous layer was washed with chloroform (50 ml) and the chloroform extracts were combined, dried and concentrated. The resultant solid was washed with pentane (40 ml), filtered off and dried to give the title compound (3.71 g, 89% yield) as crystals (mp. 126°–7° C.). T.l.c. in Solvent C, $R_f$ 0.38. $^1$H-nmr, δ:1.35 (s, 3H), 1.42 (s, 3H), 1.42 (quintet, J=7.2 Hz, 2H), 1.61–1.82 (m, 6H), 2.19 (t, J=7.5 Hz, 2H), 2.81 (d, J=12.8 Hz, 1H), 2.90 (dd, J=12.8 Hz, J=4.8 Hz, 1H), 3.10–3.16 (m, 1H), 3.31–3.36 (m, 2H), 3.48 (d, J=5.2 Hz, 2H), 3.57 (t, J=5.4 Hz, 2H), 3.71 (dd, J=8.2 Hz, J =6.2 Hz, 1H), 4.05 (dd, J=8.1 Hz, J=6.4 Hz, 1H), 4.25–4.33 (m, 2H), 4.48–4.53 (m, 1H), 5.46 (br.s, 1H), 6.28 (br.s, 1H), 6.53 (br.s, 1H). Mass spectrum (+FAB), m/z 416.3 (M$^+$·+1).

1-O-(4,4'-dimethoxytrityl)-3-O-(N-Biotinyl-3-aminopropyl)glycerol (IV)

N-biotinyl-3-aminopropyl solketal (III) (2.50 g, 6 mmole) was dissolved in a mixture of tetrahydrofuran (12 ml) and 1M hydrochloric acid (12 ml). The solution was left for 0.5 h and then absolute ethanol (12 ml) was added. The solution was concentrated, the residue was dissolved in absolute ethanol (12 ml) and concentrated again. The resultant product was dried by co-evaporation with pyridine (2×12 ml) to give an oil (2.46 g) which was redissolved in dry pyridine (24 ml) and 4,4'-dimethoxytrityl chloride (2.03 g, 6 mmole) added in a two portions with stirring. Stirring was continued for 15 min and the resultant solution was left for 1 hour. Absolute ethanol (12 ml) was added and the solution was concentrated. The residue was dissolved in chloroform (60 ml) and washed with saturated sodium bicarbonate solution (30 ml). The aqueous layer was washed with chloroform (30 ml) and the chloroform extracts were combined, dried and evaporated to an oil (528 g). The product was chromatographed on a silica column (120 g) eluting with acetonitrile/methanol (9:1) and then acetonitrile/methanol (4:1). Fractions containing a single component were collected and evaporated to dryness to yield the title compound (2.55 g, 63% yield) as a foam. T.l.c. in Solvent D, $R_f$ 0.39. $^1$H-nmr, δ:1.36–1.42 (m, 2H), 1.61–1.73 (m, 6H), 2.12–2.20 (m, 2H), 2.62 (d, J=12.8 Hz), 2.79–2.86 (m, 1H), 3.03—3.21 (m, 3H), 3.28–3.34 (m, 2H), 3.46–3.58 (m,4H), 3.77 (s, 6H), 3.93–3.96 (m, 1H), 4.15–4.24 (m, 1H), 4.35–4.41 (m, 1H), 5.43 (br.s, 1H), 6.61 (br.s, 1H), 6.78 (br.s, 1H), 6.78–6.82 (m, 4H), 7.18–7.43 (m, 9H). Mass Spectrum (+FAB), m/z 678.4 (M$^+$·+1).

1-O-(4,4'-dimethoxytrityl)-3-O-(N-biotinyl-3-aminopropyl) glyceryl 2-O-(N,N-diisopropylamino)cyanoethyl phosphite (V).

1-O-(4,4'-dimethoxytrityl)-3-O-(N-biotinyl-3-aminopropyl)glycerol (IV) (1.36 g, 2 mmole) was dissolved in dry tetrahydrofuran (4 ml) and N,N-diisopropylethylamine (0.52 ml, 3 mmole) was added. Then a solution of 2-cyanoethyl N,N-diisopropylaminochlorophosphite (0.47 g, 2 mmole) in dry tetrahydrofuran (1 ml) was added dropwise with stirring.

The reaction mixture was left for 1 h, filtered, and the filtrate was diluted with ethyl acetate (100 ml). The resultant solution was washed with 0.5M phosphate buffer pH 7.0 (2×20 ml), dried and concentrated. The residue (1.92 g) was chromatographed on a silica column (60 g) eluting with methylene chloride/methanol (39:1) and then methylene chloride/methanol (19:1) both containing 1% triethylamine. Two fractions were collected. The faster eluting product was evaporated to gave a foam (1.10 g) which was dissolved in toluene (10 ml) and precipitated into pentane (200 ml). The precipitate was washed with pentane (200 ml), collected by centrifugation, and dried. The title compound. (1.02 g, 58% yield) was obtained as a fine powder. T.l.c. in Solvent E, $R_f$ 0.33. $^1$H-nmr, δ:1.01–1.18 (m, 12H), 1.39 (quintet, J=7.2 Hz, 2H), 1.62–1.70 (m, 6H), 2.07–2.14 (m, 2H), 2.45 (t, J=6.5 H2, 1H), 2.63 (t, J=6.5 Hz, 1H), 2.65 (d, J=13.0 Hz, 1H), 2.87 (dd, J 12.8 Hz, J=4.8 Hz, 1H), 3.07–3.34 (m, 5H), 3.47–3.75 (m, 8H), 3.77 (s, 3H), 3.88 (s, 3H), 4.07–4.13 (m, 1H), 4.24–4.29 (m, 1H, 4.43–4.48 (m, 1H), 5.04 (br.s, 1H), 5.74 (br.s, 1H), 6.22 (br.d, J=18.4 Hz, 1H), 6.78–6.83 (m, 4H), 7.18–7.45 (m, 9H). $^{31}$P-nmr, δ: 6.09, 6.12, 7.61, 7.63. Mass Spectrum (+FAB) 876.4 (M$^+$·−1). Elemental analysis, found: C, 63.10; H, 7.62: N, 7.84; calculated for $C_{46}H_{64}N_5O_8P$: C, 6292; H, 7.35; N. 7.98. Hplc using isocratic elution at 90% buffer B showed two closely eluting peaks corresponding two two pairs of diastereoisomers ($R_t$ 4.82 and 5.16 min).

Fractions containing the slower eluting product were evaporated to dryness to give unreacted starting compound IV (0.44 g, 32% recovery).

N-Fluorenylmethoxycarbonyl-L-tyrosine benzyl ester (VI)

L-Tyrosine benzyl ester p-toluenesulphonate salt (11.09 g 25mmole) was dissolved in dry pyridine (125 ml). The solution was cooled in an ice water bath and then 9-fluorenylmethyl-chloroformate (6.47 g 25mmole) was added with stirring. Stirring was continued for 1 hour at 0° C. and for 1 hour at room temperature. The reaction mixture was concentrated, dissolved in toluene (50 ml) and concentrated once more to give an oil (24.0 g). Crystallization from acetonitrile (50 ml) gave an initial crop of 6.85 g. The filtrate was concentrated and the resultant oil was dissolved in chloroform (200 ml) and washed with 0.5M hydrochloric acid (50 ml). The aqueous layer was extracted with chloroform (2×50 ml) and the chloroform extracts were combined, dried and evaporated to dryness. The resultant crystalline solid (6.77 g) was combined with the first crop and recrystallized from acetonitrile (60 ml) to yield the title compound (10.38 g, 84% yield): mp. 150°–1° C. T.l.c. in Solvent F, $R_f$ 0.48. $^1$H nmr ($d_6$ DMSO), δ: 285–2.93 (m, 2H), 3.32 (d, J=12.2 Hz, 1H), 4.18–4.25 (m, 4H), 5.09 (s, 2H), 6.25 (d, J=8.4 Hz, 2H), 7.03 (d, J=84 Hz, 2H), 7.26–7.44 (m, 8H), 7.63–7.67 (m, 2H), 7.87–7.93 (m, 3H), 9.25 (m, 1H). Mass spectrum (+FAB), m/z 494.2 (M$^+$·1).

N-Fluorenylmethoxycarbonyl-O-[bis (2-cyanoethyl)-phosphate]-L-tyrosine benzyl ester VII)

N-Fluorenylmethoxycarbonyl-L-tyrosine benzyl ester (VI) (7.41 g, 15 mmole) and 1H-tetrazole (1.58 g, 22.5 mmole) were dissolved in dry acetonitrile (225 ml) and then a solution of bis(2-cyanoethyl)-N,N-(diisopropylamino) phosphine (6.10 g, 22.5 mmole) in dry acetonitrile (22.5 ml) was added dropwise with stirring. The reaction mixture was left for 1 hour and then 50% 3-chloroperbenzoic acid (5.16 g, 15 mmole) was added with stirring and cooling by use of a water bath. Stirring was continued at room temperature for 0.5 hour and the solution was concentrated to an oil (13.50 g). The oil was dissolved in chloroform (450 ml) and washed with saturated sodium bicarbonate solution (225 ml). The chloroform solution was dried, evaporated to dryness to give an oil (14.80 g). Crystallization from a mixture of methylene chloride (60 ml) and diethyl ether (120 ml) gave the title compound (8.80 g, 86% yield): mp. 103°–4° C. T.l.c in Solvent A, $R_f$ 0.44. $^1$H nmr, δ: 2.65–2.73 (m, 2H), 4.19 (t, J=6.8 Hz, 1H), 4.28–4.47 (m, 6H), 4.68 (dt, J=12.1 Hz and J=5.7 Hz, 1H), 5.12 (d, J=12.1 Hz, 1), 5.19 (d, J=12.1 Hz, 1H), 5.36 (d, J=12.1 Hz, 1H), 6.97 (d, J=8.3 Hz, 2H), 7.07 (d, J=8.3 Hz, 2H), 7.27–7.43 (m, 9H), 7.57 (d, J=7.0 Hz, 2H), 7.76 (d, J=7.4 Hz, 2H). $^{31}$P nmr, δ: 148.60. Mass spectrum (+FAB), m/z 680.3 (M$^+$·1).

N-Fluorenylmethoxycarbonyl-O-[bis(2-cyanoethyl)-phosphate]-L-tyrosine (VIII)

N-Fluorenylmethoxycarbonyl-O-[bis(2-cyanoethyl) phosphate]-L-tyrosine benzyl ester (VIII) (6.80 g, 10 mmole) was dissolved in a mixture of 95% ethanol (200 ml) and ethyl acetate (200 ml) and 10% palladium on charcoal (1.0 g) was added. The suspension was stirred under hydrogen until nearly all the substrate was gone (T.l.c. assay). The reaction mixture was filtered and the filtrate was concentrated. The resultant oil (6.20 g) was dissolved in a 1% solution of sodium carbonate (200 ml) and the solution was shaken with diethyl ether (100 ml). The aqueous solution was acidified with citric acid to pH4 and the resultant suspension was extracted with ethyl acetate (200 ml). The organic phase was dried and evaporated to give the title compound (3.83 g, 65% yield) as a solid foam. T.l.c. in Solvent G, $R_f$ 038. $^1$H nmr, δ: 2.71 (t, J=6.0 Hz, 4H), 3.13 (d, J=5.3 Hz, 2H), 4.20 (t, J=6.7 Hz, 1H), 430–4.51 (m, 6H), 4.65 (dt, J=12.0 Hz and J=5.4 Hz, 1H), 5.48 (d, J=12.1 Hz, 1H), 7.13, (s,4D, 7.28–7.43 (m, 4H), 7.58 (d, J=7.2 Hz, 2H, 7.77 (d, J=7.4 Hz, 2H). $^{31}$P nmr, δ: –148.85. Mass spectrum (+FAB), m/z 590.2 (M$^+$·+1).

N-Fluorenylmethoxycarbonyl-O-[bis(2-cyanoethyl)-phosphate]-L-tyrosine pentafluorophenyl ester (IX)

N-Fluorenylmethoxycarbonyl-O-[bis(2-cyanoethyl)-phosphate]-L-tyrosine (VIII) (2.95 g, 5 mmole) was dissolved in dry dioxane (20 ml) and a solution of pentafluorophenol (1.02 g, 5.5 mmole) in dry dioxane. (5 ml) was added. Then dicyclohexylcarbodiimide (1.13 g, 5.5 mmole) was added with stirring. Stirring was continued for 1 hour and the resultant suspension was filtered. The filtrate was concentrated to an oil (4.18 g) which was dissolved in chloroform (100 ml) and washed with saturated sodium bicarbonate solution (50 ml). The organic phase was dried and concentrated to an oil (3.52 g). The product was chromatographed on a silica column (60 g) eluting with chloroform/ethanol (39:1) and then chlorofrom/ethanol (19:1). Fractions containing a single component were collected and evaporated to dryness to yield the title compound (3.10 g, 82% yield) as a solid foam. T.l.c in Solvent A, $R_f$ 0.33. $^1$H nmr, δ: 2.74 (t, J=6.0 Hz, 4H), 3.27 (d, J=5.8 Hz, 2H), 4.21 (t, J=6.6 Hz, 1H), 4.32–4.48 (m, 6H), 4.97–5.02 (m, 1H), 5.45 (d, J=85 Hz, 1H), 7.20 (s, 4H), 7.28–7.43 (m, 4H), 756–7.59 (m, 2H), 7.77 (d, J=7.4 Hz, 2H). $^{31}$P nmr, δ: –148.67. Mass spectrum (+FAB), m/z 756.1 (M$^+$·+1).

N-[N-Fluorenylmethoxycarbonyl-O-[bis(2-cyanoethyl)-phosphate]-L-tyrosinyl)-3-aminopropyl solketal (X)

N-Fluorenylmethoxycarbonyl-O-[bis(2-cyanoethyl)-phosphate]-L-tyrosine pentafluorophenyl ester (IX) (3.02 g, 4 mmole) was dissolved in dry DMF (20 ml). Then a solution of 3-aminopropyl solketal (II) (0.91 g 4.8 mmole) in dry DMF (8 ml) was added dropwise with stirring. The reaction mixture was left for 0.5 hours and then concentrated to an oil (5.61 g) which was dissolved in chloroform (80 ml) and washed with saturated sodium bicarbonate solution (40 ml). The organic phase was dried and concentrated to an oil (4.10 g). The product was chromatographed on a silica column (100 g) eluting with chloroform/ethanol (39:1) and then chloroform/ethanol (19:1). Fractions containing a single component were evaporated to dryness to give the title compound (2.60 g, 86% yield) as a thick oil. T.l.c. in Solvent A, $R_f$ 0.26. $^1$H nmr, δ: 1.40 (s, 3H, 1.65 (s, 3H), 1 87–1.90 (m, 2H), 2.76 (t, J=6.1 Hz, 4H), 2.95–3.11 (m, 2H), 3.32–3.56 (m, 9H), 4.16–4.20 (m, 1H), 4.32–4.40 (m, 7H, 5.63–5.82 (m, 1H), 6.56–6.81 (m, 1H), 7.11–7.16 (m, 4H), 7.28–7.43 (m, 4H), 7.56 (d, J=7.4 Hz, 2H), 7.76 (d, J=7.4 Hz, 2H). $^{31}$P nmr, δ: –148.65, –148.49.

N-[N-Fluorenylmethoxycarbonyl-O-[bis(2-cyanoethyl) phosphate]-L-tyrosinyl]-3-aminopropyl solketal (X) (2.28 g, 3 mmole) was dissolved in a mixture of tetrahydrofuran (12 ml) and 1M hydrochloric acid (6 ml). The solution was left for 1 hour and then absolute ethanol (12 ml) was added. The solution was concentrated, the residue was dissolved in absolute ethanol (12 ml) and concentrated again. The resultant product was dried by co-evaporation with pyridine (2×6 ml) to give an oil (2.20 g) which was redissolved in dry pyridine (12 ml) and 4,4'-dimethoxytritylchloride (1.02 g, 3 mmole) was added with stirring. Stirring was continued for 15 mins and the resultant solution was left for 1 hour. Absolute ethanol (6 ml) was added and the solution was concentrated. The residue was dissolved in chloroform (60 ml) and washed with saturated sodium bicarbonate solution (30 ml). The organic phase was dried and evaporated to an oil (432 g). The product was chromatographed on a silica column (90 g) eluting with methylene chloride/methanol (39:1) and then methylene chloride/methanol (19:1). Fractions containing a single component were collected and evaporated to dryness to yield the title compound (2.15 g, 70% yield) as a solid foam. T.l.c. in Solvent H, $R_f$ 028. $^1$H nmr, δ: 1.61–1.67 (m, 2H), 2.66 (q, J=5.7 Hz, 2H), 276 (t, J=6.0 Hz, 2H), 3.03–3.14 (m, 4H), 3.29–3.52 (m, 7H), 3.74 (s, 3H), 3.79 (s, 3H), 3.88 (br s, 1H), 4.23–4.40 (m, 8H), 5.56–5.82 (m, 1H), 656–6.68 (m, 1H), 6.78 (d, J=8.9 Hz, 2H, 6.82 (d, J=9.0 Hz, 2H), 7.13–7.54 (m, 19H), 7.72–7.78 (m, 2H). $^{31}$P nmr, δ: –148.59, –148.57. Mass spectrum (+FAB), m/z 1022.6 (M$^+$·).

1-O-(4,4'-dimethoxytrityl)-3-O-(N-[N-fluorenylmethoxycarbonyl-O-[bis(2-cyanoethyl) phosphate]-L-tyrosinyl]-3-aminopropyl)glyceryl 2-O-(N,N-diisopropylamino)(2-cyanoethyl)phosphite (XII).

1-O-(4,4'-dimethoxytrityl)-3-O-(N-(N-fluorenylmethoxycarbonyl-O-[bis(2-cyanoethyl)phosphate]-L-tyrosinyl)-3-aminopropyl)glycerol (XI) (2.04 g, 2 mmole) was dissolved in dry tetrahydrofuran (4 ml) and N,N-diisopropylethylamine (0.70 ml, 4 mmole) was added. Than a solution of 2-cyanoethyl N,N-diisopropylaminochlorophosphite (0.71 g, 3 mmole) in dry tetrahydrofuran (2 ml) was added dropwise with stirring. The reaction mixture was left for 1 hour, filtered and the filtrate was diluted with ethyl acetate (100 ml). The resultant solution was washed with 0.5M phosphate buffer pH 7.0 (2×20 ml), dried and concentrated. The residue (2.52 g) was chromatographed on a silica column (80 g) eluting with methylene chloride/ethyl acetate (3:1) and then methylene chloride/ethyl acetate (1:1), both containing 1% of 2,6-lutidine. Fractions containing a single component were collected and evaporated to dryness. The resultant oil (1.62 g) was dissolved in toluene (16 ml) and product precipitated with pentane (320 ml). The precipitate was washed with pentane (2×320 ml), collected by centrifugation, and dried. The title compound (1.08 g, 44% yield) was obtained as a fine powder. T.l.c. in Solvent I, $R_f$ 0.26. 1H nmr, δ: 1.14–1.33 (m, 12H), 1.56–1.75 (m, 2H), 2.54–2.79 (m, 6H), 2.93–3.26 (m,6H), 3.38–3.61 (m, 7H), 3.76 (s, 6H), 4.05–4.42 (m, 10H), 5.44–5.60 (m, 1H), 6.21–6.33 (m, 1H), 6.79–6.83 (m, 4H), 7.27–7.57 (m, 19H), 7.76 (d, J=7.6 Hz, 2H). $^{31}$P nmr, δ: −148.65, −148.64, 7.41, 7.68, 7.96. Mass spectrum (+FAB), m/z 1223.9 (M$^+$+1). Elemental analysis, found : C, 64.70, H, 6.34, N, 6.92; calculated for $C_{66}H_{76}N_6O_{13}P_2$: C, 64.81, H, 6.26, N, 6.87. Reversed-phase HPLC using isocratic elution at 90% Buffer B showed two closely eluting peaks corresponding to two pairs of diastereomers ($R_t$ 6.14 and 6.86 min).

Oligonucleotide Assembly

Oligonucleotides were assembled using an Applied Biosystems 380B 3-column DNA Synthesiser following manufacturers recommendations with the cyanoethyl phosphoramidite procedure. 0.2 μmole scale columns were used throughout. For couplings with biotinyl phosphoramidite V or phosphotyrosinyl phosphoramidite XII a 0.2M concentration in anhydrous acetonitrile was used and the coupling wait time was increased to 300 secs (compared to 30 secs for normal nucleotide coupling). Both these modifications were necessary to obtain high coupling yields for phosphoramidites V and XII. In each final coupling cycle, the Trityl ON configuration was used. After assembly, the oligonucleotides were cleaved from the support using concentrated ammonia at room temperature using the manufacturer's end procedure cycle. The ammoniacal solution was then heated to 60° C. in a sealed tube for 5 h and evaporated to dryness. The residue was dissolved in 0.3 ml acetic acid/water (8:2) and after 20 minutes at room temperature the mixture was evaporated to dryness. To the residue was added water (0.5 ml) and the resultant suspension filtered. The aqueous solution now contained the deprotected oligonucleotide ready for h.p.l.c. purification.

EXAMPLE 2

A) Synthesis of Fluorescein Phosphoramidite
Fluorescein-5-isothiocyanate-3',6'-dibenzoate Fluorescein-5'-isothiocyanate (5 g, 12.85 mmole) was dissolved in dry pyridine (15 ml). Benzoyl chloride (3 ml, 3.61 g, 25.7 mmole) was added dropwise over 15 minutes without external cooling and the reaction mixture was stirred in the dark overnight. The reaction mixture was stirred in the dark overnight. The reaction was then partitioned between ethyl acetate (150 ml) and 5% aqueous sodium bicarbonate (150 ml). The organic layer was washed twice more with bicarbonate (150 ml each) and with brine (150 ml). TLC over silica (ethyl acetate/pentane 2/1 v/v) showed only one fluorescein containing spot Rf 0.75.

Aminopropyl Glycerol

3-Aminopropyl solketal (2.43 g, 12.8 mmole) was dissolved in THF (30 ml) and aqueous hydrochloric acid (1M, 30 ml) was added. After 1 hour at room temperature TLC (acetonitrile/methanol/triethlyamine 80/18/2) indicated that all starting material Rf 0.33 had been hydrolyzed to the diol Rf ca.0.0 (detection by ninhydrin spray). THF was evaporated in vacuo and the aqueous residue was applied to a Dowex 50 ion exchange column (100 ml, H form). The resin was washed with water to remove all Cl ion and the desired amine was eluted with aqueous ammonia. The ammonia soution was evaporated to remove all volatile material and the aqueous residue used for subsequent reactions without further purification.

Dibenzoyl-fluorescein aminopropyl-glyceryl thiourea

Fluorescein-5-isothiocyanate-3',6'-dibenzoate (0.11 mmole) was dissolved in ethyl acetate/acetonitrile (4/1 v/v) and stirred as a solution of aminopropyl-glycerol in water (0.11 mmole, 1 ml) was added. After 1 hour stirring at room temperature, TLC (ethyl acetate/pentane 2/1) showed complete conversion of starting material (Rf 0.75) to material Rf ca.0.0 TLC in a different system (acetonitrile/ethanol 4/1) showed one fluorescein containing spot Rf 0.76. The reaction mixture was washed with 5% sodium bicarbonate (2×20 ml) and brine (2×20 ml), dried over anhydrous sodium sulphate and evaporated to dryness to yield a yellow oil.

Dimethoxytrityl-dibenzoyl-fluorescein aminopropyl-glyceryl thiourea

Dibenzoyl-fluorescein aminopropyl-glyceryl thiourea (82 mg, 0.11 mmole) was azeotroped with pyridine (2×20 ml) and dissolved in pyridine. Dimethoxytrityl chloride (60 mg, 0.16 mmole) dissolved in pyridine (10 ml) was slowly added to the stirred solution over 40 minutes at room temperature and the reaction stirred for a further 20 minutes. The reaction mixture was concentrated under vacuum and partitioned between ethyl acetate (50 ml) and 5% aqueous sodium bicarbonate (2×50 ml). TLC (ethyl acetate/pentane 2/1 v/v) showed conversion of all polar material to spot Rf 0.60. The organic extract was dried over anhydrous sodium sulphate, filtered and evaporated. Residual pyridine was removed by azeotrope with toluene (2×10 ml) and the material applied to a silica gel column which was eluted with a gradient of ethyl acetate in pentane (20% to 60%). Fractions containing pure material were combined and evaporated to dryness to yield the product as a pale yellow foam (28 mg). Reverse phase hplc C18 column, 15 cm) showed one single peak retention 8.58 minutes (detector 254 nm). Buffer A=0.1M triethylammonium acetate 1 Buffer B=acetonitrile. Solvent program 80% B to 95% over 10 minutes, flow 1.0 ml/min, then isocratic for 5 minutes.

Dimethoxytrityl-dibenzoyl-fluorescein aminopropyl-glyceryl thiourea diisopropylamino cyanoethyl phosphoramidite The dimethoxytrityl compound (1.93 g 1.85 mmole) was azeotroped with acetonitrile (3×50 ml) and dissolved in dry dichloromethane (50 ml). Cyanoethyl-tetraisopropyl-phosphorodiamidite (0.613 g, 2.03 mmole) was added followed by diisopropylammonium tetrazole (0.158 g, 0.925 mmole). The mixture was left to react 1 hour at room temperature and was then quenched by addition of 50 ml 5% aqueous sodium bicarbonate. The organic layer was dried by addition of anhydrous sodium sulphate, filtered and evaporated. The resulting yellow oil was dissolved in dry dichloromethane (3 ml) and the product precipitated by addition of pentane (25 ml). The supernatant was decanted and the residual oil dried under high-vacuum to give an off-white foam (1.1 g). Hplc analysis reveals the product as a pair of diastereomers retention times 3.99, 4.44 minutes (C18 column, 15 cm, 95% acetonitrile, 5% 1M triethylammonium acetate, isocratic, flow 1 ml/minute).

B) Use of a fluorescein phosphoramidite to prepare oligonucleotides for use as hybridization probes.

Materials and Methods

Oligonucleotides were assembled using an Applied Biosystems 394-08 4 column DNA synthesizer following manufacturers recommendations with the cyanoethyl phosporamidite procedure. The 0.2 umole scale was used throughout. For couplings using the fluorescein phosphoramidite a 0.2M concentration in anhydrous acetonitrile was used and the coupling wait extended to 300 seconds. Three parallel syntheses were performed of the M13 17-mer forward sequencing primer d(GTAAAACGACGGCCAGT) bearing 1, 7 and 8 fluorescein labels at the 5'end. In each final coupling the trityl-on configuration was used.

After synthesis, detritylation was performed as in example 1.

Purification of the oligonucleotides was by reverse-phase HPLC on a Ultrasphere-ODS column (Sum, 4.6 mm×15 cm)

(Beckman Instruments) using gradients of buffer A (0.1M ammonium acetate) and buffer B (20% buffer A/80% acetonitrile) at flow rates of 1 ml/minute.

M13-mp8 single stranded DNA was spotted (1 ul) onto Hybond N-nylon membrane (Amersham code 2020B) in dilutions from 20–0.0125 ng/ul in $H_2O$. A negative control of 50 ng/ul of denatured herring sperm DNA was also spotted out. The filters were then baked for 2 hours at 80° C.

Prehybridization of the filters was performed in 0.5% block reagent (ECL-Oligonucleotide labelling system, Amersham, RPN 2111), 0.1% N-lauroylsarcosine (sodium salt), 0.02% SDS, 5×SSC for 30 minutes at 42° C. Hybridizations using the probes labelled with 1 and 7 fluorescein molecules at 20 ng/ml were then carried out for 2 hours at 42° C. in the same buffer. Filters were then washed for 2×15 minutes in 1×SSC,, 0.1% SDS at 42° C., followed by a 5 minute wash in 2×SSC at room temperature.

Detection of the fluorescein labelled probes involved blocking of the filters in 1% block reagent (ECL-Oligonucleotide labelling system, Amersham, RPN 2111), 100 mM Tris-HCL, 150 mM NaCl, pH 7.5 for 60 minutes at 42° C. The filters were then incubated for 30 minutes at room temperature in sheep anti-fluorescein antibody conjugated to horseradish peroxidase (ECL 3'-tailing system, Amersham, RPN 2130) diluted 1 in 1000 in block buffer. After 4×5 minute washes in 100 mM Tris-HCl. 400 mM NaCl, pH 7.5 at room temperature, detection was carried out using the enhanced chemiluminescent (ECL) detection reagents (Amersham, RPN 2105) followed by exposure to Hyperfilm ECL autoradiography film (Amersham, RPN 2103) for 1 hour.

Results

Efficiency of addition of the fluorescein phosphoramidite averaged 92% as judged by the release of the dimethoxytrityl cation before subsequent coupling steps.

Purification of the fluorescein labelled oligonucleotide by reverse phase HPLC revealed that the fluorescein caused a retardation in mobility compared to unlabelled oligonucleotide. Retention times for the 1 and 7 labelled oligonucleotides were 17 and 29 minutes respectively, compared to 16 minutes for the unlabelled oligonucleotide. The oligonucleotide bearing 8 fluoresceins gave the same retention time as for the 7 fluorescein probe.

In the detection of single stranded M13 DNA, greater sensitivity was observed for the probe bearing 7 fluoresceins than for the probe bearing a single fluorescein. Dection limits after a 1 hour exposure to film were 12.5 pg and 100 pg for the 7 and 1 fluorescein probes respectively.

EXAMPLE 3

Materials and Methods

Radiolabelling of the biotinylated oligonucleotides: The biotinylated oligonucleotides (17-mers) were synthesized as described in example 1. The oligonucleotides corresponded to the sequence of the universal M13 sequencing primer (d(GTAAAACGACGGCCAGT)). Batches of this oligonucleotide were labelled at the 5'-end with 1, 2 or 8 biotins using the biotinyl phosphoramidite reagent. After complete deprotection, the three 17-mers had been purified using reverse phase chromatography. A 17-mer, with no biotin label, was obtained from an M13 sequencing system (Amersham code N 4502). The four 17-mers were adjusted to 10 pmoles/5 $\mu$l and were boiled for 5 min then rapidly chilled on ice. They were then labelled at the 3' end using $^{32}$P-dCTP (Amersham Code PB 10205) and a 3'-end Labelling Kit (Amersham Code N 4020). The radiolabelled 17-mers were then purified from unincorporated dNTPs by centrifugation down a Sephadex-G25 spin-column.

Capture assay for the radiolabelled 17-mers: The assays were performed in white, microtitre plates (DynaTech) with removable wells. The wells were coated with aliquots (200 ul of a solution of 20 $\mu$g ml$^{-1}$) of either streptavidin (Amersham Code RPN 1041) in TBS (per liter: Tris base, 2.42 g; NaCl, 8 g; 1M HCl, 3.8 ml; pH 7.6) or a mouse monoclonal antibody against biotin in 0.1M carbonate/bicarbonate buffer (pH 9.5) and incubated at 4° C. overnight. The wells were then washed three times in TBS with 0.1% (v/v) Tween-20 (TBST). Aliquots (200 $\mu$l) of blocking solution (TBS with 0.1% (w/v) bovine serum albumin) were then added and the plate incubated for 1 h at 37° C. After washing three times with TBST solution, aliquots (200 $\mu$l) of oligonucleotide solution were added to each appropriate well and the plate re-incubated for 1 h at 37° C. Following incubation, the wells were again washed three times in TBST and the final wash solution removed. Each well was then placed in separate scintillation vials and assayed by Cerenkov counting. % Capture was determined using the following equation:

$$\% \text{ Capture} = \frac{\text{Count in well after capture assay}}{\text{Original count added per well}} \times 100\%$$

RESULTS

The objective of the experiment was to monitor capture of an oligonucleotide labelled with biotinyl phosphoramidite residues using either streptavidin or an anti-biotin antibody to capture the biotin-oligonucleotide onto the solid phase of a microtitre well. By 3'-radiolabelling the oligonucleotides the efficiency of capture could be determined using scintillation counting of the wells.

Experiment 1

Figure 8:
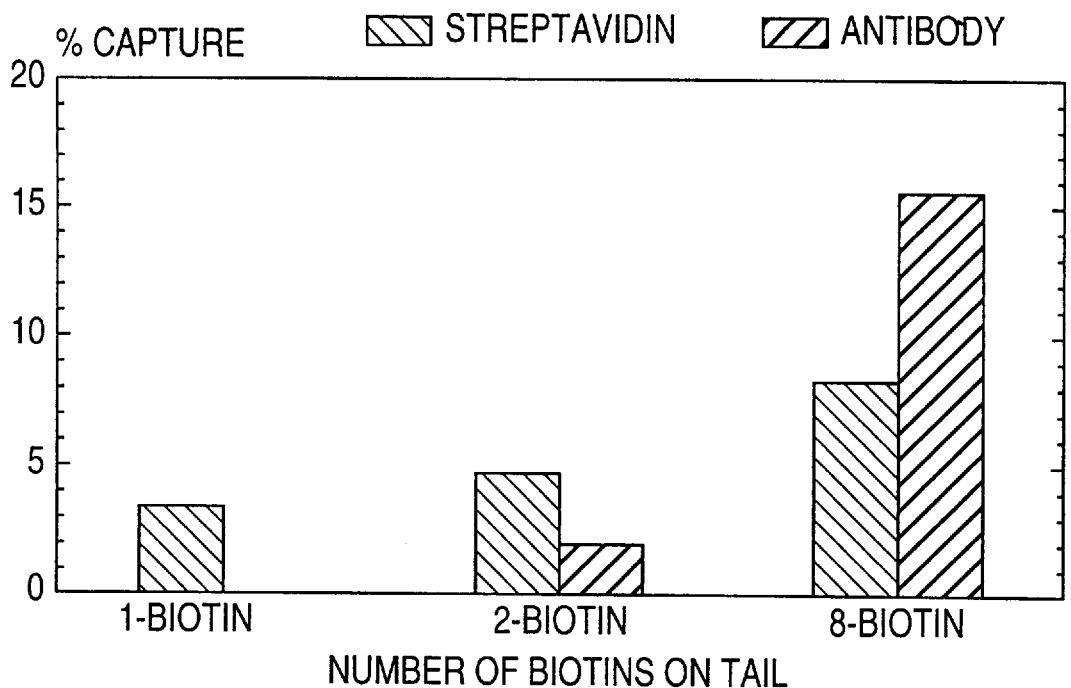
FIG. 8 shows the effect of biotin tail length on efficiency of DNA capture—Experiment 1.

In this experiment approximately 2×10$^{13}$ radiolabelled oligonucleotide molecules were added per well. The results suggested that capture was occurring and that with the anti-biotin antibody there was a correlation between increasing biotin tail length and its efficiency of capture (FIG. 8). Although there also appeared to be a similar correlation with streptavidin as the capturing agent, the increase in capture efficiency with increased biotin tail length was less than that with antibody capture.

Experiment 2

Figure 9:
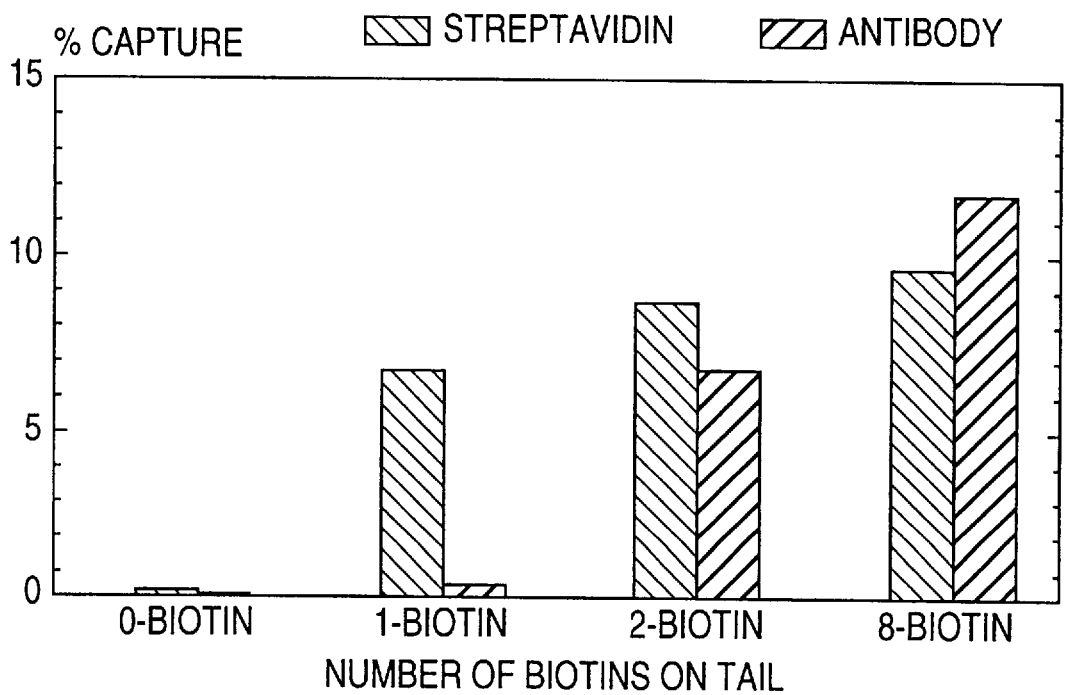
FIG. 9 shows the effect of biotin tail length on efficiency of DNA capture—Experiment 2.
Figure 10:
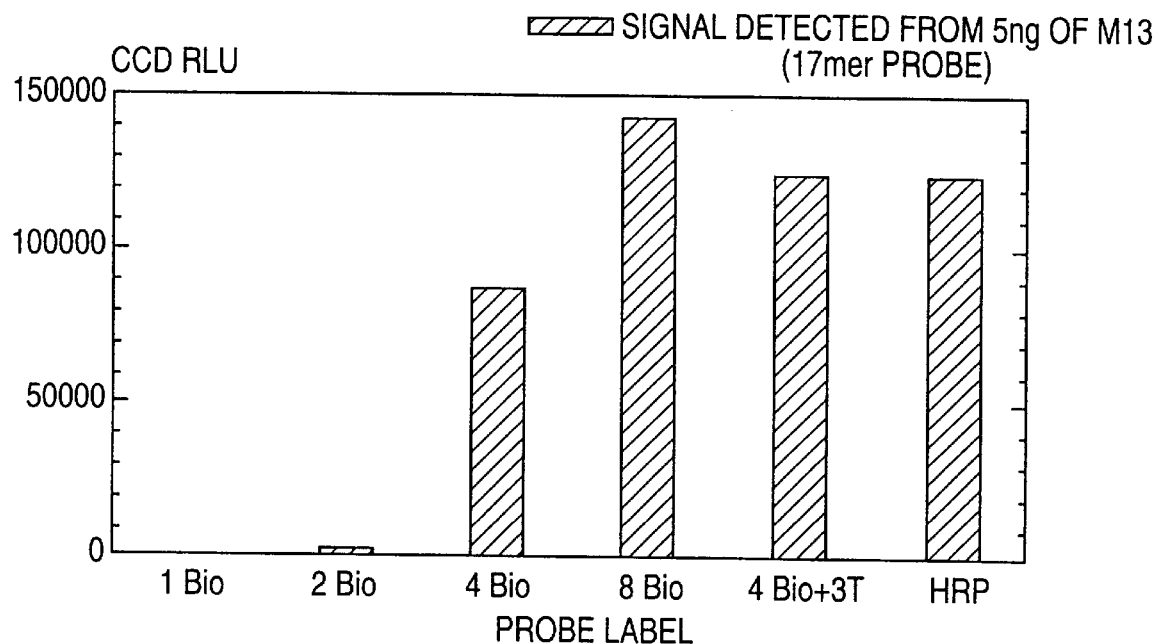
FIG. 10 shows signal strength for ECL detection of 5 ng of M13 DNA for each of five biotinylated probes.

In this experiment approximately 2.4×10$^{12}$ oligonucleotide molecules were added per well. The results from experiment 1 were verified and the biotin-labelled oligonucleotides were captured at levels significantly above background (oligonucleotide with no biotin label) suggesting that the biotin label was being captured (FIG. 9).

EXAMPLE 4

Solid Phase sequencing of DNA generated by the Polymerase Chain Reaction (PCR)

The protocol is based on the method of Hultmann T., et al (1989) Nucleic Acids Research 17, pp. 4937–4946. Specific target DNA is amplified by PCR using one biotinylated primer and one non-biotinylated primer. The amplified DNA is captured via the biotin by streptavidin linked to a solid phase (in this example, a magnetic bead). The non-biotinylated strand is then removed by alkali. Either the bound strand or the non-bound strand can then be sequenced using standard protocols.

Materials and Methods
Amplification by the Polymerase Chain Reaction

Biotinylated primer oligonucleotides were synthesised as described in Example 1. The template DNA (typically 1–2 pmols of target sequence) was amplified in 50 μl containing 10 mM Tris-HCl, pH9.5, 50 mM NaCl, 3 mM MgCl2, 0.01% NP-40, 0.05% gelatin, 250 μM each of dATP, dCTP, dGTP and dTTP, 5 pmoles of biotinylated primer 1, 5 pmols of non-biotinylated primer 2 and 2μ of Taq polymerase (Amersham code T0303Y). The reactions were cycled for 30 cycles of 94° C. for 45 seconds, 45° C. for 45 seconds and 72° C. for 2 minutes.

Preparation of Single Stranded Template

Immediately prior to use, the streptavidin coated beads (Dynal, M-280 streptavidin) were washed for 2×5 minutes in 0.1M NaCl. The beads were resuspended after washing at a concentration of 10 mg/ml in 0.1M NaCl.

50 μl of washed beads were added to a fresh tube and the beads separated. The completed PCR mix was used to resuspend the beads and the tube was incubated for 30–60 minutes at room temperature, with mixing. The beads were then separated and washed with 200 μl of water.

Single stranded template was prepared by incubating the beads coated with PCR DNA in 20 μl of 0.15M NaOH for 5 minutes at room temperature. The beads were then separated and washed once with 200 μl of 0.15M NaOH and then twice with 200 μl of water. The beads were finally resuspended in 30 μl of water.

Sequencing of Solid Phase DNA

The solid phase bound template was sequenced exactly as single stranded template using the T7 polymerase Multiwell microtitre plate sequencing system (Amersham, code RPN1590).

The sequencing reactions were denatured prior to loading on a standard 6% sequencing gel by heating at 95° C. for 5 minutes. At this point, the beads can be separated and the supernatant loaded on the gel.

Electrophoresis and subsequent processing of the sequencing gel were exactly as standard protocols.

EXAMPLE 5

Use of Primers Labelled with Biotinyl or Phosphotyrosinyl Phosphoramidite in Sequencing Reactions Materials and Methods Primer oligonucleotides were labelled with biotin or phosphotyrosine as in Example 1. The primers were used at a concentration of 0.12 OD/ml (~0.8 μM) in row 3 of a T7 Multiwell plate. All other procedures were as standard for the T7 Multiwell System (Amersham, code RPN1590).

EXAMPLE 6

Direct Enhanced Chemiluminescence (ECL) Detection of Blotted Sequencing Ladders Using Labelled Primers Materials and Methods
Sequencing Reactions The reactions were performed as in example 5. Single stranded M13mp8 (Amersham, code N4526) was used as template at 3 μg per sequencing reaction. ($^{35}$S]dATPαS was included in the sequencing reaction to assess the quality of the sequencing ladder before and after transfer.

Blotting of Sequencing Gel

The preparation, pre-running and running of the sequencing gel was exactly as standard protocols.

After electrophoresis, the sequencing ladder was blotted as follows. The glass plates were separated and a sheet of filter paper was placed on the gel surface such that no air bubbles were trapped between gel and paper. The gel was then lifted from the glass plate and placed paper side down on a clean, flat surface.

A piece of nitrocellulose membrane (Hybond C-extra, Amersham, code RPN303E) was prewet in 50 mM ammonium acetate (AmAc) and was then carefully laid onto the gel, again taking care that no air bubbles were trapped between the gel and membrane. A sheet of filter paper was then laid on top of the membrane, again ensuring that all air bubbles were removed. Excess membrane and filter paper were then trimmed from the edges of the gel.

The gel sandwich was then inverted and placed on a stack of paper towels that had previously been soaked in 500 mM AmAc and dried (in an oven at 50° C.). On top of the gel, towels soaked in 50 mM AmAc were layered. A flat perspex sheet and weights of about 1 kg were then placed on top of the wet towels. The transfer was allowed to proceed overnight.

After blotting, the membrane and gel were separated and the DNA was fixed to the membrane by placing the blot on a vacuum gel drier for 2 hours at 80° C. The blot was then autoradiographed to assess the efficiency of transfer of the sequencing ladder.

Detection of the Sequencing Ladder Using Streptavidin-HRP and ECL

The membrane with the transferred sequencing ladder was treated as follows.

The membrane was blocked by incubation for 1 hour in PBS-Tween (0.05%) containing 5% non-fat milk. After washing for 6×5 minutes in PBS-Tween (0.05%), the membrane was incubated for 60–90 minutes with Streptavidin-biotinylated HRP complex (RPN1051) diluted 1:1000 in PBS-Tween (0.05%).

After washing for 6×5 minutes in PBS-Tween (0.05%), the sequencing ladder was detected using ECL as described in the ECL Gene Detection System (Amersham, code RPN2101).

EXAMPLE 7

Use of Biotinyl and Phosphotyrosinyl Phosphoramidites for Preparing Oligonucleotides for Use as Hybridisation Probes (Extracted from Misiura, K. et al (1990) Nucleic Acids Research, 18: pp.4345–54)

Materials and Methods

M13 sequencing primers labelled with biotin or phosphotyrosine were prepared as in Example 1.

M13mp19 single-stranded DNA was spotted on pre-wet (water, then 1M ammonium acetate solution) nitrocellulose filters (Schleicher and Schuell) in serial dilutions in 10 mM Tris HCl (pH 7.4), 5 mM NaCl, 0.1 mM EDTA (amounts 0.05–50 ng). The filters were baked at 80° C. for 1 hour and washed in 6XSSC, 0.2% BSA, 0.2% PVP 40, 0.2% Ficoll 400, 0.2% SDS at 60° C. for 10 mins. After brief rinsing in 6XSSC, hybridisation was carried out in solutions of biotinylated or phosphotyrosinylated oligomers (10 nM) at 37° C. for 2 hours. Filters were washed in 2XSSG, 0.1% SDS twice for 1 minute and then for 1 minute in 2XSSC.

Quantitative detection of biotinylated probes involved blocking of the filter with 5% w/v reconstituted milk powder in TBST (Tris buffered saline plus 0.05% Tween 20) for 1 hour, incubation with a mouse monoclonal antibody against biotin (0.1 µg/ml in TBST), washing with TBST (6×5 mins) and then incubation with sheep anti-mouse IgG-horseradish peroxidase conjugate (Amersham, code NA 931) at a 1/1000 dilution in TBST. After washes with TBST (6×5 mins) and TBS (1×5 min), detection was carried out using the enhanced chemiluminescent (ECL) detection reagents (Amersham, code RPN 2105). The still moist filters were photographed and quantitated using a CCD camera (600 second exposures). Control 17-mer oligonucleotide directly linked to horseradish peroxidase was prepared using the ECL oligonucleotide labelling and detection system (Amersham code, RPN 2111/2113).

Phosphotyrosine-labelled probes were detected quantitatively using the ECL method. Primary detection was by a mouse monoclonal antibody against phosphotyrosine (0.5 µg/ml) and the secondary antibody was sheep anti-mouse IgG conjugated to horseradish peroxidase (Amersham, Code NA931) used at 1/1000 dilution.

Results

As the number of biotin residues in the probe was increased, there was a substantial increase in signal strength in detection of M13 DNA (FIG. 14). Spacing of biotin with thymidinyl residues resulted in a 50% increase in signal strength compared to the unspaced probe at this M13 DNA concentration. In addition, the sensitivity of detection using either the (bio)$_8$-17 probe or the spaced (bio-dT)$_3$-bio-17 probe was very similar to that obtained with the same 17-mer directly conjugated to horseradish peroxidase.

There was also a significant increase in signal strength obtained as the number of phosphotyrosinyl residues was increased (FIG. 11), although the effect was less pronounced than in the case of biotinylated oligonucleotides. Spacing of phosphotyrosine with thymidinyl residues resulted in a slight decrease in signal strength compared to the unspaced probe.

Using the ECL system and biotinylated or phosphotyrosinylated probes, a linear logarithmic response was observed between the amount of light produced and the amount of M13 DNA spotted on the filter. (Misiura, K. et al, (1990) Nucleic Acid Research, 18, pp.4345–54).

References

1. Agrawal, S. A., Christodoulou, C. and Gait, M. J. (1986) Nucleic Acids Res., 14, 6229–6245.
2. Connolly, B. A. (1987) Nucleic Acids Res., 15, 3131–3139.
3. Coull, J. M., Weith, H. L. and Bischoff, R. (1986) Tetrahedron Letters, 27, 3991–3994.
4. Kansal. V.K., Huynh-Dinh, T. and Igolen, J. (1988) Tetrahedron Letters, 29, 5537–5540.
5. Gillam, I. C. and Tener, G. M. (1986) Anal. Biochem., 157, 199–206.
6. Gebeyehu, G., Rao, P. Y., SooChan, P., Simms, D. A., and Klevan, L. (1987), Nucleic Acids Res., 15, 4513–4534.
7. Ruth, J. R. (1984) DNA, 3, 123.
8. Haralambidis, J., Chai, M. and Tregear, G. W. (1987) Nucleiic Acids Res., 15, 4857–4876.
9. Roget, A., Bazin, H. and Teoule, R. (1989) Nucleic Acids Res., 17, 7643–7651.
10. Langer, P. R., Waldrop, A. A. and Ward, D. C. (1981) Proc. Natl. Acad. Sci. USA, 78,6633–6637.
11. Nelson, P. S., Sherman-Gold, R., and Leon, R. (1989) Nucleic Acids Res., 17, 7179–7186.
12. Haralambidis, J., Angus, K., Pownall. S., Duncan, L., Chai, M. and Tregear, G. W. (1990) Nucleic Acids Res., 18, 501–505.
13. Alves, A. M., Holland, D. and Edge, M. D. (1989) Tetrahedron Letters, 30. 3089–3092.
14. Cocuzza, A. J. (1989) Tetrahedron Letters, 30, 6287–6290.
15. Satoh, T., Suzuki, S., Suzuki, Y., Miyaji, Y, and Imai, Z. (1969) Tetrahedron Letters, 4555–4558.
16. Sinha, N. D., Biernat, J., McManus, J. and Köster, H. (1984) Nucleic Acids Res., 12, 4539–4557.
17. Caruthers, M. H. (1985) Science, 230, 281–285.
18. Duckworth, M. L., Gait, M. J., Goelet, P., Hong, G. F., Singh, M., and Titmas, R. (1981) Nucleic Acids Res., 9, 1691–1706.
19. Carpino, L. A. and Han, G. Y. (1970) J. Amer. Chem. Soc., 92, 5748–5749.
20. Bayer, E. A. and Wilchek, M. (1974) Methods Enzymol., 34, 265–267.
21. Uhlmann, E. and Engels, J. (1986) Tetrahedron Letters, 27, 1023–1026.
22. McCormick, D. D. and Ruth, J. A (1970) Methods Enzymol., 18A, 383–385.

We claim:

1. A phosphoramidite derivative of the following formula:

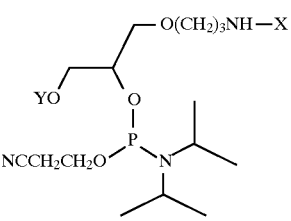

(V)

wherein

X=a reporter group, and

Y=a protecting group.

2. A phosphoramidite derivative as claimed in claim 1, wherein there is a linker arm of variable length between the reporter group X and the rest of the molecule.

3. A phosphoramidite derivative as claimed in claim 1, wherein X is a hapten or other detectable moiety.

4. A phosphoramidite derivative as claimed in claim 1, wherein Y is 4,4'-dimethoxytrityl.

5. A method for the single or multiple labelling of synthetic oligonucleotides and which comprises the use of a phosphoramidite ligand as claimed in claim 1.

6. A method for the single or multiple labelling of synthetic oligonucleotides and which comprises the use of a phosphoramidite ligand as claimed in claim 1, wherein the labelling with said phosphoramidite ligand occurs at the 5' end or the 3' end of the oligonucleotide or at any internal position along the chain.

* * * * *